United States Patent
Colavin et al.

(10) Patent No.: US 11,462,299 B2
(45) Date of Patent: Oct. 4, 2022

(54) MOLECULAR EVIDENCE PLATFORM FOR AUDITABLE, CONTINUOUS OPTIMIZATION OF VARIANT INTERPRETATION IN GENETIC AND GENOMIC TESTING AND ANALYSIS

(71) Applicant: Invitae Corporation, San Francisco, CA (US)

(72) Inventors: Alexandre Colavin, Menlo Park, CA (US); Carlos L. Araya, Palo Alto, CA (US); Jason A. Reuter, Palo Alto, CA (US)

(73) Assignee: INVITAE CORPORATION, San Francisco, CA (US)

( * ) Notice: Subject to any disclaimer, the term of this patent is extended or adjusted under 35 U.S.C. 154(b) by 851 days.

(21) Appl. No.: 16/162,889

(22) Filed: Oct. 17, 2018

(65) Prior Publication Data

US 2019/0189246 A1    Jun. 20, 2019

Related U.S. Application Data

(60) Provisional application No. 62/573,458, filed on Oct. 17, 2017.

(51) Int. Cl.
*G16B 30/00* (2019.01)
*G16B 20/00* (2019.01)
(Continued)

(52) U.S. Cl.
CPC .............. *G16B 30/00* (2019.02); *G06K 9/623* (2013.01); *G06K 9/6262* (2013.01); *G06N 20/00* (2019.01);
(Continued)

(58) Field of Classification Search
CPC .......... G16B 30/00; G16B 5/00; G16B 40/00; G16B 50/10; G16B 20/00; G16B 50/00;
(Continued)

(56) References Cited

U.S. PATENT DOCUMENTS

| 5,780,236 A | 7/1998 | Dove et al. |
| 6,949,692 B2 | 9/2005 | Dove et al. |

(Continued)

FOREIGN PATENT DOCUMENTS

| WO | WO 2015/027085 A1 | 2/2015 |
| WO | WO 2016/154584 A1 | 9/2016 |

(Continued)

OTHER PUBLICATIONS

International Search Report and Written Opinion of the International Searching Authority directed to related International Patent Application No. PCT/US2018/056304, dated Dec. 27, 2018, 9 pages.

(Continued)

*Primary Examiner* — Jerry Lin
(74) *Attorney, Agent, or Firm* — Sterne, Kessler, Goldstein & Fox P.L.L.C.

(57) ABSTRACT

Disclosed herein are system, method, and computer program product embodiments for optimizing the determination of a phenotypic impact of a molecular variant identified in molecular tests, samples, or reports of subjects by way of regularly incorporating, updating, monitoring, validating, selecting, and auditing the best-performing evidence models for the interpretation of molecular variants across a plurality of evidence classes.

20 Claims, 6 Drawing Sheets

(51) Int. Cl.

| | |
|---|---|
| *G16B 40/00* | (2019.01) |
| *G16B 5/00* | (2019.01) |
| *H04L 9/06* | (2006.01) |
| *H04L 67/10* | (2022.01) |
| *G16B 50/00* | (2019.01) |
| *G16B 20/20* | (2019.01) |
| *G16B 50/10* | (2019.01) |
| *G06N 20/00* | (2019.01) |
| *G06K 9/62* | (2022.01) |
| *H04L 9/00* | (2022.01) |

(52) U.S. Cl.
CPC ............... *G16B 5/00* (2019.02); *G16B 20/00* (2019.02); *G16B 20/20* (2019.02); *G16B 40/00* (2019.02); *G16B 50/00* (2019.02); *G16B 50/10* (2019.02); *H04L 9/0637* (2013.01); *H04L 9/0643* (2013.01); *H04L 67/10* (2013.01); *H04L 9/50* (2022.05)

(58) Field of Classification Search
CPC ...... G06N 20/00; G06K 9/623; G06K 9/6262; H04L 9/0637; H04L 9/0643; H04L 67/10
See application file for complete search history.

(56) References Cited

U.S. PATENT DOCUMENTS

| | | |
|---|---|---|
| 6,955,883 B2 | 10/2005 | Margus et al. |
| 7,702,468 B2 | 4/2010 | Chinitz et al. |
| 7,993,833 B2 | 8/2011 | Begovich et al. |
| 8,655,599 B2 | 2/2014 | Chinitz et al. |
| 11,344,572 B2 | 5/2022 | Bishop et al. |
| 2012/0310539 A1 | 12/2012 | Crockett et al. |
| 2013/0338012 A1 | 12/2013 | Sulem et al. |
| 2015/0106112 A1 | 4/2015 | Jackson et al. |
| 2016/0072800 A1 | 3/2016 | Soon-Shiong et al. |
| 2016/0306923 A1 | 10/2016 | Van Rooyen et al. |
| 2016/0314245 A1 | 10/2016 | Silver et al. |
| 2016/0364522 A1 | 12/2016 | Brendan et al. |

FOREIGN PATENT DOCUMENTS

| | | |
|---|---|---|
| WO | WO 2016/172464 A1 | 10/2016 |
| WO | WO 2019/079464 A1 | 4/2019 |

OTHER PUBLICATIONS

International Preliminary Report on Patentability directed to related International Patent Application No. PCT/US2018/056304, dated Apr. 21, 2020.

Extended European Search Report and Written Opinion for European Application No. 18868620.8, European Patent Office, dated Jul. 7, 2021, 12 pages.

Boudellioua et al., "Semantic prioritization of novel causative genomic variants," PLOS Computational Biology, 13(4):1-21, Apr. 17, 2017.

Yandell et al., "A probabilistic disease-gene finder for personal genomes," *Genome Research*, 21(9):1529-42, Sep. 2011.

Forsman, "Effects of genotypic and phenotypic variation on establishment are important for conservation, invasion, and infection biology" (pp. 302-307) (Jan. 7, 2014).

McLaren et al., "The Ensembl Variant Effect Predictor", (pp. 1-14) (Jun. 6, 2016).

Notice of Allowance directed to related U.S. Appl. No. 16/756,802, dated Jun. 16, 2022; 10 pages.

MOLECULAR EVIDENCE PLATFORM FOR AUDITABLE, CONTINUOUS OPTIMIZATION OF VARIANT INTERPRETATION IN GENETIC AND GENOMIC TESTING AND ANALYSIS

BACKGROUND

Molecular tests, such as genetic and genomic tests, are increasingly important diagnostic tools in a wide-array of clinical settings, from an individual's risk of neonatal seizures, abnormal heart rhythm (e.g., arrhythmia) or predisposition to developing cancers. The determination of the phenotypic impact (e.g., both clinical and non-clinical, including, but not limited to, pathogenicity, functionality, or relative effect) of a molecular variant—such as a genotypic (sequence) variant—identified within a subject is often the cornerstone of clinical molecular testing. The validity and utility of molecular testing can require that such determinations (e.g., often known as variant classifications) be evidence-based, objective, and systematic (Yandell et al. Genome Res. 2011 September; 21(9): 1529-42).

Driven in large-part by next-generation sequencing (NGS) technologies, rapid advances in genetic and genomic technologies have led to dramatic increases in the volume (e.g., market adoption), diversity, and scope (e.g., sequence information assayed) of genetic and genomic tests. In conjunction, the number of variants of unknown significance has dramatically increased, affecting the sensitivity and specificity of clinical genetic and genomic tests.

A preponderance of molecular variants of unknown (e.g., clinical or non-clinical) phenotypic impact is a feature of nearly all genes and all populations, including many clinically-significant genes. Even in the most heavily studied clinical genes and conditions, existing knowledge of the clinical significance of molecular variants often remains sparse. For example, in the case of the BRCA1 gene, a large, international consortium of clinical geneticists, molecular pathologists, and BRCA1 experts have defined classifications for 108 non-synonymous molecular variants, providing clinical significance support for ~0.7% of the 16,200 possible non-synonymous single-nucleotide genotypic (sequence) variants in BRCA1 (BRCA Exchange). As a consequence, the vast majority of molecular variants identified in modern gene-panel and genomic tests have no known phenotypic impact or clinical significance. For example, recent reports indicate modern hereditary cancer gene panel tests can find as many as ninety-five variants of unknown significance per known disease-causing variant (95:1 ratio) (Maxwell et al., 2016).

In addition to their limited availability, existing knowledge and classifications regarding the (clinical or non-clinical) phenotypic impact of molecular variants are continuously evolving. For example, ~50% of BRCA1 non-synonymous single-nucleotide genotypic (sequence) variants in a large public repository of clinical significance classifications (ClinVar) have conflicting classifications, and a consensus-based definition of truth can lead to a classification instability of ~11% over a 12 month window (Landrum et al., 2015). In many genes, and for many conditions, the growth in conflicting classifications can outpace growth of novel, consensus-derived classifications (Landrum et al., 2015). In addition, consistent advances in the understanding of genomic variation, disease etiology, and molecular pathology and epidemiology, among other characteristics, has lead to a consistent evolution of the corresponding "truth set" of variant impacts and classifications.

During variant interpretation and review, a genetic or genomic test provider can request access to evidence surrounding a variant, gene, condition, and case via a variant interpretation support system. Owing to the high numbers of genetic variants of unknown clinical significance, genetic and genomic test providers routinely rely on a diverse array of evidence types to determine the phenotypic impact (e.g., clinical or non-clinical) of molecular variants of otherwise unknown effect identified in subjects and tests. A variant interpretation support system can include one or more lines of supporting evidence, including, but not limited to, data from computational predictors, mutational hotspots, functional assays, and population metrics, among others. However, owing to the consistent growth and shifting nature of variant classifications—which form the basis of "truth sets" for the evaluation of evidence models—the computed performance metrics (e.g., diagnostic, classification, regression accuracy, etc.) for any evidence model are frequently outdated. In addition, a reliance on a wide array of evidence models developed (e.g., computed, assayed, or aggregated) and evaluated in distinct settings (e.g., with frequently disjoint truth set definitions) often results in incoherent evaluation metrics among evidence models. Together these factors complicate the evaluation and use of evidence models as support for variant interpretation. As a consequence, a variant interpretation support system can not be able to reliably compare the performance of evidence models whereby evaluations are based on different data, within or between their different classes.

In addition, the variant interpretation support system can contain evidence models that have been evaluated with different performance metrics (e.g., diagnostic, classification, regression accuracy, etc.) of interest. Thus, the variant interpretation support system can be unable to systematically and objectively compare the performance of the different evidence models. While continued scientific work and publications routinely generate new evidence models, the lack of uniform "truth set" definitions, lack of synchronous updating, and biases in their performance evaluation (e.g., as might arise from authorship interests), can limit the inherent quality and utility of the evidence generated and their associated performance metrics. As a consequence, a variant interpretation support system cannot reliably compare the performance of evidence models that were evaluated with different performance metrics, within or between their different classes.

In addition to these issues with evidence evaluation, the consistent growth and shifting nature of existing classifications (e.g., and hence truth sets) affects the robustness of evidence models, which often require a supervised learning step for generation. As truth sets continuously evolve, both the evaluation and generation of evidence can require updating. As such, the variant interpretation support system can not have access to the most up-to-date evidence models possible. For example, the variant interpretation support system can contain a computational predictor that yields a prediction for a genetic variant that is inconsistent with the known phenotypic impact of the variant, as was learned after the predictor was generated.

Finally, the variant interpretation support system can be incapable of confirming that an evidence model was generated at a given moment in time, or generated with a given dataset. A genetic and genomic test provider that obtains supporting evidence from the variant interpretation support system can therefore be unable to guarantee that performance metrics (e.g., diagnostic, classification, regression accuracy, etc.) for the evidence model are up-to-date, robust, and computed exclusively on disjoint data, e.g., on the basis of variants not used (or available) in the generation of the model.

Accordingly, there is a need for new or improved variant interpretation supports systems that overcome the shortcomings of the currently available systems.

BRIEF SUMMARY

The present disclosure provides a computer implemented method, the method comprising (i) recording an evidence model comprising evidence data, wherein the evidence data describes a predicted phenotypic impact of a molecular variant for a target entity; (ii) evaluating validation performance data for the evidence model based on production data; (iii) generating a hash value of supporting data for the evidence model, wherein the supporting data comprises the evidence data, and the generation of the hash value enables prospective evaluation of the evidence data in response to receiving test data for the evidence model; (iv) in response to receiving the test data for the evidence model, evaluating test performance data for the evidence model based on the evidence data and the test data; (v) ranking the evidence model in a set of evidence models for the target entity based on the validation performance data or the test performance data; and (vi) in response to a query for the predicted phenotypic impact of the molecular variant for the target entity from a variant interpretation terminal, providing the predicted phenotypic impact using a best-performing evidence model for the target entity based on the ranking.

In some aspects, the target entity comprises a functional element, molecule, or molecular variant, and a phenotype of interest.

In some aspects, the recording further comprises generating the evidence model based on the production data using a machine learning technique. In some aspects, the recording further comprises importing the evidence model or the evidence data. In some aspects, the method further comprises generating the supporting data from at least one of the evidence data, the production data, the test data, the validation performance data, or the test performance data.

In some aspects, the generation of the hash value enables evaluation of content of the supporting data and a time of creation of the supporting data. In some aspects, the method further comprises receiving the production data from a clinical knowledgebase.

In some aspects, the evaluating the validation performance data further comprises (i) calculating, using the evidence model and a model validation technique, a phenotype impact score for the molecular variant of the target entity in the production data; and (ii) generating the validation performance data based on the phenotype impact score using a performance metric of interest.

In some aspects, the evaluating the test performance data further comprises (i) calculating, using the evidence model and a model validation technique, a phenotype impact score for the molecular variant of the target entity in the test data; and (ii) generating the test performance data based on the phenotype impact score using a performance metric of interest.

In some aspects, the method further comprises storing the hash value of the supporting data in a database, wherein the database associates the hash value with the supporting data. In some aspects, the method further comprises inserting the hash value into a distributed data structure.

In some aspects, the method further comprises providing an audit record to a variant interpretation terminal, wherein the audit record references an entry for the supporting data in the distributed data structure, and the audit record enables the variant interpretation terminal to audit content of the supporting data and a time of creation of the supporting data. In some aspects, the distributed data structure is a blockchain data structure. In some aspects, the distributed data structure is a distributed feed.

The present disclosure also provides a variant interpretation terminal system, comprising: a memory; and at least one processor coupled to the memory and configured to: send a support query to a variant interpretation system for supporting data for an evidence model meeting a set of performance metrics for a target entity; receive the supporting data and an associated auditing record for the supporting data from the variant interpretation system; send an audit query to a distributed data structure, wherein the audit query comprises the auditing record for the supporting data; receive a certificate of validation for the auditing record from the distributed database in response to the sending of the audit query; and determining a data state of the supporting data at a point in time based on the auditing record.

In some aspects, the at least one processor is configured to: compute a hash value of the supporting data for the evidence model; and determine the hash value matches a hash value in the auditing record for the supporting data for the evidence model. In some aspects, the target entity comprises a functional element, molecule, or molecular variant, and a phenotype of interest.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Figure 1:
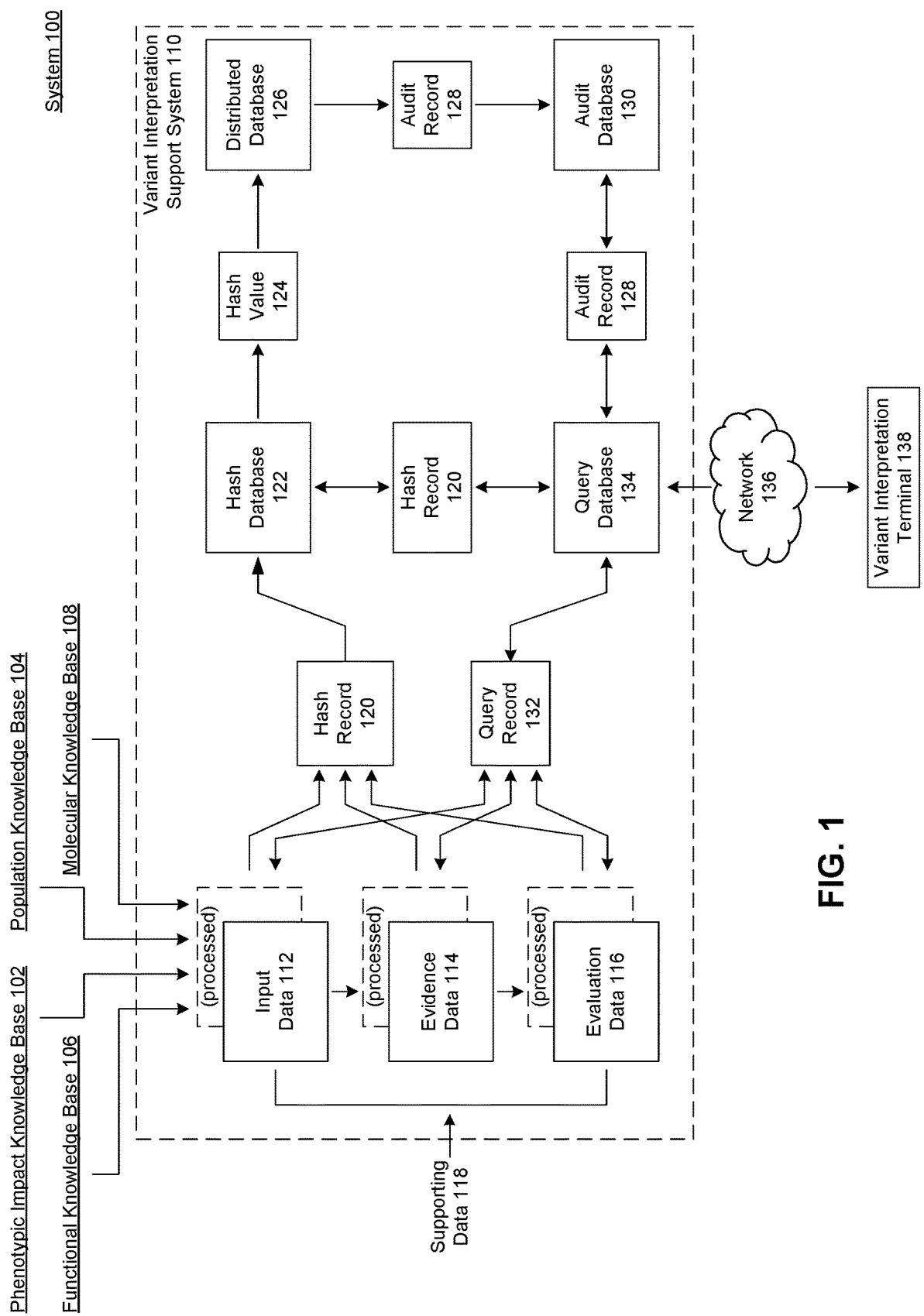
FIG. 1 is a block diagram of a system for providing an optimal set of evidence models for describing or predicting the phenotypic impacts of molecular variants for one or more functional elements (or molecules), phenotypes, contexts, or set of variants of interest at a given time, according to some aspects.

Provided herein are system, apparatus, device, method and/or computer program product aspects, and/or combinations and sub-combinations thereof, for optimizing the determination of the phenotypic (e.g., clinical or non-clinical) impact (e.g., pathogenicity, functionality, or relative effect) of molecular variants identified in molecular tests, samples, or reports of subjects—such as genotypic (sequence) variants identified in genetic and genomic tests, samples, or reports—by way of regularly incorporating, updating, monitoring, validating, selecting, and auditing the best-performing supporting evidence models for the interpretation of molecular variants across a plurality of evidence classes.

In some aspects, each evidence model can constitute a system of unique molecular variants and their associated (e.g., clinical or non-clinical) phenotypic impact (e.g., pathogenicity, functionality, or relative effect). As would be appreciated by a person of or ordinary skill in the art, evidence models can be derived using a range of methods, techniques, and data sources, including both computational and experimental models, or combinations thereof (e.g., training computational predictors, computing mutational hotspots, defining population allele frequency thresholds, or measuring the functional impact of variants in molecular or cellular assays). For example, variant scores or predictions from a computational predictor can be accessed to determine the likely (e.g., clinical or non-clinical) phenotypic impact of a genotypic (sequence) variant of unknown significance. For example, when interpreting the clinical significance of genotypic (sequence) variants in MSH2 (e.g., a gene encoding an established tumor suppressor protein), a computational predictor can determine that certain genotypic (sequence) variants (or molecular variants) of unknown clinical significance can likely increase the lifetime risk of Lynch Syndrome in subjects carrying the variant.

In some aspects, a variant interpretation support system can integrate and utilize many different lines of evidence (e.g., evidence models) to determine the (e.g., clinical or non-clinical) phenotypic impact of molecular variants identified in molecular diagnostic tests, samples, or reports of subjects. However, in some aspects, a variant interpretation support system can lack comparable performance metrics (e.g., raw accuracy, balanced accuracy—such as Matthew's Correlation Coefficient (MCC), true positive rate (TPR) or sensitivity, true negative rate (TNR) or specificity, positive predictive value (PPV), and negative predictive value (NPV)) that are specific to the diagnostic context of the test for each and all evidence models. This is because the variant interpretation support system can contain evidence models that were generated or evaluated using different truth sets at different times, or assessed using different performance metrics.

Moreover, owing to the continuous growth and changes in the knowledge and classification of the (e.g., clinical or non-clinical) phenotypic impacts of molecular variants, in some aspects, the variant interpretation support system can not contain the most up-to-date possible evidence model, and can contain evidence models that are in conflict with the (e.g., clinical or non-clinical) phenotypic impacts learned after the evidence models were generated. Thus, the variant interpretation support system can not reliably provide the most appropriate, and up-to-date evidence models to a genetic and genomic test provider.

Thus, what is needed is a way for a variant interpretation support system to regularly incorporate (e.g., generate or import), monitor, update, validate, select, distribute and audit different evidence models to ensure use of the best-performing evidence models for the interpretation of molecular variants in the context of specific individuals, families, or populations, at a given moment in time. In some aspects, the variant interpretation support system can provide consistent evaluation(s) by systematically (1) defining truth sets describing the phenotypic impacts (e.g., labels) of molecular variants and (2) scoring evidence models across a set of performance metrics using test data of the (e.g., clinical or non-clinical) phenotypic impacts of molecular variants. As would be appreciated by a person of ordinary skill in the art, test data can refer to disjoint data specifying the (e.g., clinical or non-clinical) phenotypic impacts of molecular variants not used in the data for generation of the evidence models (e.g., the production data). The variant interpretation support system can need to also provide an independent way to verify that a provided evidence model was generated with or without the use of particular data, by either (1) directly confirming the presence or absence of the data in the production data, or (2) inferring the absence of particular data in the production data by comparing timestamps of evidence model incorporation (e.g., generation or import) with the known or accepted timestamps for the availability of specific data.

In some aspects—at a specific point in time—the objective selection of evidence models can meet specific performance criteria for use in the interpretation of (e.g., clinical or non-clinical) phenotypic impacts of molecular variants—such as genotypic (sequence) variants—in one or more (e.g., coding or non-coding) functional elements (e.g., protein-coding genes, non-coding genes, molecular domains such as protein or RNA domains, promoters, enhancers, silencers, regulatory binding sites, origins of replication, etc.) in the (e.g., nuclear, mitochondrial, etc.) genome(s), or their derivative molecules. As would be appreciated by a person of ordinary skill in the art, a genotypic (sequence) variant can be a single-nucleotide variant (SNV), a copy-number variant (CNV), or an insertion or deletion affecting a coding or non-coding sequence (or both) in the genome. As would be appreciated by a person of ordinary skill in the art, a molecular variant can be a single-amino acid substitution in a protein molecule, a single-nucleotide substitution in a RNA molecule, a single-nucleotide substitution in a DNA molecule, or any other molecular alteration to the cognate sequence of a biological polypeptide. As would be appreciated by a person of ordinary skill in the art, a phenotype can be one or more clinical or non-clinical observable characteristics and can be assessed in the context of specific populations, age groups, genders, tissues, or mutation types (e.g., somatic, germline inherited, germline de novo). Specifically, in some aspects, a variant interpretation support system can regularly incorporate (e.g., generate or import) or update evidence models for the interpretation of molecular variants in (e.g., coding or non-coding) functional elements in genomes or derivative molecules in the context of specific phenotypes or collections of phenotypes. In some aspects, the variant interpretation support system can regularly evaluate the comparative performance of evidence models against new (e.g., novel or changing) data of the (e.g., clinical or non-clinical) phenotypic impacts of molecular variants. In some aspects, the variant interpretation support system can reliably ensure the objective selection of evidence models meets specific performance criteria for one or more (e.g., coding or non-coding) functional elements and phenotypes at the time of variant interpretation.

FIG. 1 is a block diagram of a system 100 for providing an optimal set of evidence data 114 for describing or predicting the phenotypic impacts of molecular variants for one or more functional elements (or molecules), phenotypes, contexts, or set of variants of interest at a given time, according to some aspects. System 100 includes data from various knowledge bases (e.g., phenotypic impact knowledge base 102, population knowledge base 104, functional knowledge base 106, or molecular knowledge base 108), a variant interpretation support system 110, a network 136, and variant interpretation terminal 138. As would be appreciated by a person of ordinary skill in the art, some aspects of system 100 can provide a multiplicity of evidence models for one or more functional elements and phenotypes, as well as evidence models for specific contexts. For example, in some aspects, system 100 can use one or more evidence models of diverse classes (e.g., computational predictors, mutational hotspots, functional assays, biophysical simulations, population allele frequency thresholds, or other).

In some aspects, a (e.g., clinical or non-clinical) phenotypic impact knowledge base 102 includes one or more molecular variant information databases. In some aspects, a molecular variant information database can include information of molecular variants and their associated phenotypes or phenotypic impacts. Phenotype and phenotypic impact associations of molecular variants can be derived from the observation of molecular variants in affected and unaffected individuals, families, and populations, or representative experimental models. For example, clinical testing can establish that a molecular variant is pathogenic or benign on the basis of a statistically significant rate of observation in affected or unaffected individuals, respectively.

In some aspects, knowledge bases (e.g., phenotypic impact knowledge base 102) used to generate input data 112 can be public databases, in which the information is open to the public. In some aspects, a knowledge base can be a private (e.g., proprietary) database in which the information is only accessible to the company or entity that created the database, or those permitted to access the database.

In some aspects, variant interpretation support system 110 includes a database of input data 112, a database of evidence data 114, a database of evaluation data 116, a database of hash records 120 (e.g., a hash database 122), and a database of audit records 128 (e.g., an audit database 130). In some aspects, input data 112 (e.g., data from variants, residues (e.g., positions), and molecules of (e.g., coding or non-coding) functional elements in the genome) is imported to variant interpretation support system 110. Input data 112 can be either used directly as evidence data 114, or be utilized in the generation of evidence data 114 (e.g., evidence models). Evidence data 114 can describe a set of molecular variants and their associated (e.g., clinical or non-clinical) phenotypic impact (e.g., pathogenicity, functionality, or relative effect). In some aspects, the performance (e.g., accuracy) of evidence data 114 (e.g., direct or processed) can be recorded and stored in evaluation data 116. In some aspects, the hash value 124 of individual raw or processed input data 112, evidence data 114, or evaluation data 116 (or combinations thereof), collectively termed the supporting data 118 for an evidence model, are computed and stored in a hash record 120 in a hash database 122, permitting the unique association and identity verification of hash values 124 with raw or processed input data 112, evidence data 114, or evaluation data 116. In some aspects, the variant interpretation support system 110 can generate an audit record 128 by storing the hash value 124 of supporting data 118 of an evidence model (or set of evidence models) in a distributed database 126 (e.g., a blockchain, a public or private feed (e.g., Twitter® feed), or various other data structure as would be appreciated by a person of ordinary skill in the art) accessible by the variant interpretation terminal 138. In some aspects, audit records 128 are stored in an audit database 130 that associates hash values 124 and audit records 128. In some aspects, a query database 134 is accessed via network 136 and provides access to query record 132 information from supporting data 118 in response to requests for molecular variants, functional elements (or molecules), phenotypes, contexts, etcetera. In some aspects, the query database 134 provides the associated hash records 120 and audit records 128 information with the requested supporting data 118. In some aspects, a query database 134 is accessible via an application program interface (API). This feature of variant interpretation support system 110 can enable variant interpretation terminal 138 to audit the availability, date of creation, and contents of supporting data 118—e.g., input data 112, evidence data 114 (e.g., evidence models), or evaluation data 116—relating to any evidence model describing the phenotypic impacts of molecular variants for one or more functional elements (or molecules), phenotypes, contexts, or set of variants of interest at a given time. As would be appreciated by a person of ordinary skill in the art, supporting data 118 can refer to any input data 112, evidence data 114, or evaluation data 116, or derivatives thereof.

In some aspects, after incorporating (e.g., generating or importing), monitoring, updating, and validating evidence models, the variant interpretation support system 110 can follow a process for selecting and distributing variant interpretation support from evidence models that ensures the performance, accuracy, and reliability of the supporting data 118 provided to a variant interpretation terminal 138. First, this process can ensure reliable comparative evaluation of different evidence models. Second, this process can reduce the substantial time involved for the system to review, select, and provide the most performant evidence model(s). Third, this process can enable independent, automated validation of the data used for the provided evidence model(s). Finally, this process can ensure that evidence model(s) with the desired performance criteria are selected for use in variant interpretation in the variant interpretation terminal 138, at the time of request. Thus, this process offers an improved technological solution to the conventional industry practice of evidence model selection and use which is often reliant on the aggregation of evidence models from disparate sources, generated from disparate data, and evaluated against disparate data or using disparate performance metrics. Moreover, this system provides an alternative process for automatically ranking and selecting the best performing evidence model for particular functional elements and phenotypes.

This improved technological solution is necessarily rooted in the technology of incorporating (e.g., generating and importing), evaluating, auditing, and distributing evidence models, such as computational predictors, for the interpretation (e.g., classification) of molecular variants. Specifically, variant interpretation support system 110 can follow a series of steps immediately upon incorporating an evidence model. For both generated and imported evidence models, these steps can include calculating a series of performance and quality control metrics (e.g., the evaluation data 116), generating hash records 120 for supporting data 118, and generating an audit record 128 of the supporting data 118 in a distributed database 126 for future auditing purposes. These steps can establish a baseline for the comparative performance evaluation of (e.g., diverse) evidence models as a function of the growing and changing knowledge base of (e.g., clinical or non-clinical) phenotypic impacts for molecular variants of previously undetermined impact (e.g., clinical significance). In other words, these steps can enable variant interpretation support system 110 to evaluate the performance of evidence models (and associated supporting data 118 and methods for their generation), in view of only the (e.g., clinical or non-clinical) phenotypic impacts of molecular variants with novel associations.

In some aspects, variant interpretation support system 110 can utilize or trigger independent (e.g., pre-programmed) modules to directly import or process input data 112. Input data 112 can refer to variant, residue (e.g., position), and molecule data of (e.g., coding or non-coding) functional elements in the genome. Variant data can specify the (e.g., clinical or non-clinical) phenotypic impacts of molecular variants and can be derived from clinical or non-clinical observations in the affected and unaffected individuals, families and populations, or variant scores derived from computational predictors, models, or simulations, variant scores derived from functional assays and measurements, and variant scores derived from population allele frequencies. Residue data can include data describing evolutionary properties and relationships of, between, and among residues in functional elements, physicochemical properties and relationships of, between, and among residues in functional elements, functional properties and relationships of, between, and among residues in functional elements, structural properties and relationships of, between, and among residues in functional elements, and dynamic properties and relationships of, between, and among residues in functional elements. Molecule data can include data describing functional, evolutionary, structural, and dynamics information of functional elements. An example of input data 112 is data (or databases) of allele or variant frequencies observed in the general population or specific populations (e.g., data from the Exome Aggregation Consortium (Lek et al., 2016)). An example of data derived from input data 112 is a list of genotypic (sequence) variants that are likely benign due to their high frequency in the general population or specific populations. In some aspects, variant interpretation support system 110 can also store an input data identifier that uniquely identifies (e.g., raw or processed) input data 112.

In some aspects, variant interpretation support system 110 can trigger independent (e.g., pre-programmed) modules to directly import or generate evidence data 114 (e.g., predictions of the phenotypic impacts of molecular variants) from input data 112, as generated by evidence models such as computational predictors developed using machine learning methods. In some aspects, evidence data 114 can indicate the specific predictions of the phenotypic impacts of molecular variants. In some other aspects, evidence data 114 can refer to objects, algorithms, and functions that yield predictions of the phenotypic impacts of molecular variants.

In some aspects, an evidence model can be generated (e.g., trained) to predict the (e.g., clinical or non-clinical) phenotypic impacts of molecular variants using a diversity of machine learning methods and techniques. In some aspects, an evidence model (e.g., a computational predictor) for a given functional element or molecule can be specific for a phenotype and/or context. In some aspects, an evidence model (or evidence data 114 from the evidence model) can be specific to a given functional domain, specific subset of residues, or specific subset of molecular variants of a functional element, such as the set of non-synonymous single-nucleotide genotypic (sequence) variants (i.e., SNV-accessible missense mutations) in a specific protein domain of a protein-coding gene. In some other aspects, an evidence model can be specific to a group of related functional elements, such as a set of proteins of homologous structure and function. An example of (e.g., raw) evidence data 114 generated by an evidence model is a table of the probabilities of the pathogenicity of all possible non-synonymous single-nucleotide genotypic (sequence) variants in a protein-coding gene for a specific clinical phenotype. An example of (e.g., processed) evidence data 114 derived from an evidence model is a table of the predicted pathogenic or benign classifications of the 50% highest-confidence predictions from the evidence model. In some aspects, variant interpretation support system 110 can also store an evidence model identifier that uniquely identifies an evidence model and its associated the input data 112, evidence data 114, and evaluation data 116.

In some aspects, variant interpretation support system 110 stores performance and quality-control metadata (e.g., the evaluation data 116) related to an evidence model in an evaluation database. For example, variant interpretation support system 110 can compute and/or store in evaluation data 116 validation performance data corresponding to uniform sets of performance metrics (e.g., diagnostic, classification, regression accuracy, etc.) computed using production data. In some aspects, variant interpretation system 110 can leverage a cross-validation scheme to compute performance metrics using disjoint sets of molecular variants available in the production data but held-out in the generation of evidence models during training data. Similarly, variant interpretation support system 110 can compute and/or store evaluation data 116 in the form of test performance data corresponding to uniform sets of metrics of diagnostic accuracy for test data (e.g., disjoint molecular variants unavailable in the production data) at a later time. As would be appreciated by a person of ordinary skill in the art, the evaluation of performance metrics computed between phenotypic impact predictions from evidence models and the phenotypic impacts determined (or made available) at a time after evidence model generation can permit robust prospective evaluation of the performance of diverse evidence models under systematic definitions of truth sets and performance metrics. In some aspects, variant interpretation support system 110 can also store an evaluation data identifier that uniquely identifies raw or processed evaluation data 116.

In some aspects, variant interpretation support system 110 can evaluate the validation performance data of an evidence model. As would be appreciated by a person of ordinary skill in the art, variant interpretation support system 110 can evaluate the validation performance data of the evidence model in order to give an unbiased estimate of the predictive performance (e.g., accuracy) of the evidence model for the interpretation of the (e.g., clinical or non-clinical) phenotypic impacts of molecular variants at a given time. This can overcome the problem of a genetic testing provider being unable to assess the predictive performance of a specific evidence model, such as a computational predictor, due to the continuously growing and changing knowledge base of phenotypic impacts for genetic variants.

As would be appreciated by a person of ordinary skill in the art, variant interpretation support system 110 can evaluate the validation performance data of the evidence model using various model validation techniques, including for example diverse techniques that are standard in the fields of machine learning and data science. In some aspects, variant interpretation support system 110 can apply a cross-validation training/validation scheme (e.g., rotation estimation) using the evidence model production data as a model validation technique for assessing how the validation performance data of a statistical analysis (e.g., computed on subsets of the production data) will generalize to independent sets of molecular variants.

In some aspects, variant interpretation support system 110 can generate a hash record 120 by generating a hash value 124 of supporting data 118 (e.g., input data 112, evidence data 114, or evaluation data 116) related to an evidence model (or set of evidence models) and store the hash record 120 in the hash database 122. In some aspects, variant interpretation support system 110 can create a hash record 120 of the identity and labels of molecular variants in the production data. In some aspects, variant interpretation support system 110 can generate a hash record 120 of the phenotypic impact scores, probabilities, predictions and/or associated confidence estimates as generated by an evidence model. In some aspects, the hash record 120 can be stored in a hash database 122 within variant interpretation support system 110 that relates the hash value 124 to the data, or combination of data, from which the hash value 124 was calculated, as well as the hashing function used to compute the hash value 124 from the data. In some aspects, variant interpretation support system 110 can generate an audit record 128 of any supporting data 118 used to generate, monitor, or validate one or more predictions for one or more molecular variants to enable variant interpretation terminal 138 to audit diverse characteristics of the evidence model. As would be appreciated by a person of ordinary skill in the art, the hash value 124 of the data can always be regenerated given the original data and the hashing function. As would be appreciated by a person of ordinary skill in the art, a hash function that is statistically collision-resistant can be used to generate hash value 124 from supporting data 118 that uniquely identifies supporting data 118. In some aspects, variant interpretation support system 110 can generate a single hash value 124 from a combination of hash values for storage in the hash database 122, such as by computing the hash value 124 as the root of the Merkle tree with other hash values as leaves in the tree. As would be appreciated by a person of ordinary skill in the art, various hashing functions can be used to generate the hash value 124.

In some aspects, variant interpretation support system 110 can generate a hash record 120 for a set of supporting data 118 from one or more evidence models by either (1) computing the hash value 124 and storing the hash record 120 for a single data object (e.g., a compressed data object) containing all supporting data, or (2) computing the hash value 124 of the set of hash values 124 associated with one or more supporting data in the hash database 122.

In some aspects, variant interpretation support system 110 can generate an audit record 128 by storing the hash value 124 of evidence model supporting data 118 in a distributed database 126 (e.g., a blockchain, a public or private feed (e.g., Twitter® feed), or various other data structure as would be appreciated by a person of ordinary skill in the art) to enable variant interpretation terminal 138 to audit the evidence model's associated supporting data 118 (e.g., input data 112, evidence data 114, and/or evaluation data 116). In some aspects, the distributed database 126 can be immutable. In other aspects, the distributed database 126 can be behind a firewall to prevent the entity controlling variant interpretation support system 110 from modifying audit records 128. The audit record 128 can include a timestamp representing the date and time when the hash value 124 was inserted into the distributed database 126. In some aspects, the timestamp is automatically added by the distributed database 126 reflecting the precise date and time when the hash value 124 was stored. The audit record 128 can also include identifiers that uniquely identify the associated hash value 124 within the distributed database 126. The audit record 128 identifiers can also uniquely identify the corresponding data within variant interpretation support system 110. The audit records 128 can be stored in an audit database 130 within variant interpretation support system 110. The hash value 124 relates audit record 128 in the audit database 130 with the corresponding hash record 120 in the hash database 122, and the associated hash record 120 relates each hash value 124 with the corresponding, or associated supporting data 118 and hashing function(s).

In some aspects, variant interpretation support system 110 can enter the hash value 124 in a blockchain data structure, recording a corresponding audit record 128 containing all necessary information to identify the entry in the data structure. As would be appreciated by a person of ordinary skill in the art, a blockchain data structure can be a distributed database that maintains a continuously growing list of ordered blocks (e.g., which can be identified with audit records 128). Moreover, as would be appreciated by a person of ordinary skill in the art, a blockchain data structure is inherently resistant to modification of its data. Once recorded, the data in a block cannot be altered retroactively. Thus, a blockchain-based audit record 128 can be used to confirm the availability of specific data within variant interpretation support system 110 at a specific date and time. In some aspects, the availability of specific data is inferred from the unique association between a specific hash value with that specific data.

In some aspects, variant interpretation support system 110 can enter the hash value 124 in a secure, remote, independent, or third-party data structure (e.g., Twitter® feed), recording the corresponding audit record 128 containing the necessary information to identify the entry (and its date of creation). Moreover, as would be appreciated by a person of ordinary skill in the art, a secure, remote, independent or third-party data structure can be inherently resistant to modification of its data. Thus, an audit record 128 associated with a hash value 124 stored in a secure, remote, independent, or third-party data structure (e.g., Twitter® feed) can be used to confirm the availability of specific data within variant interpretation support system 110 at a specific date and time.

In some aspects, variant interpretation support system 110 can receive new data regarding the (e.g., clinical or non-clinical) phenotypic impacts of molecular variants, in some aspects, from phenotypic impact knowledge base 102. This data can include (e.g., clinical or non-clinical) phenotypic impacts for molecular variants of unknown phenotypic impacts at the time of evidence model generation, or unavailable at the time of evidence model generation. In some aspects, variant interpretation support system 110 can evaluate the phenotypic impact predictions (e.g., evidence data 114) of the evidence model against new phenotypic impacts using a uniform set of performance metrics (e.g., diagnostic, classification, regression accuracy, etc.) to determine the test performance data of the evidence model, or associated evidence data 114. In some aspects, variant interpretation support system 110 can record test performance data of evidence model updating the evaluation data 116.

In some aspects, variant interpretation support system 110 can compare test performance data and validation performance data, or their associated dispersion estimates (e.g., confidence intervals), to determine whether an evidence model, or its associated evidence data 114, meets the expected (or required) performance (or are within the expected range of performances). For example, variant interpretation support system 110 can examine whether the performance metrics achieved in test performance data meet the expected (or required) performance requirements (or are within the expected range of performances) determined in the validation performance data and associated analysis of generalizability.

In some aspects of variant interpretation support system 110, comparisons of test performance data and validation performance data apply label-flipping quality controls (e.g., recorded) in the evaluation data 116 to normalize test performance data. This feature permits the evaluation of test performance data to account for the (e.g., observed or expected) volatility of labels in the phenotypic impacts owing to the growing and changing nature of (e.g., clinical or non-clinical) phenotypic impacts in the knowledge base prior to comparisons to the validation performance data.

In some aspects, variant interpretation support system 110 can update evidence models in response to new data, as well as compute performance metrics for the disjoint set of (e.g., new) molecular variants. As would be appreciated by a person of ordinary skill in the art, various model validation techniques can be used. In some aspects, variant interpretation support system 110 can determine a test performance result based on the original phenotypic impact predictions of the evidence models using one or more performance metrics (e.g., diagnostic, classification, regression accuracy, etc.), which can comprehend both the accuracy (e.g., quality) of predictions as well as the coverage (e.g., quantity) of the possible molecular variants in a functional element (or molecule) of interest. In some other aspects, variant interpretation support system 110 can determine an updated test performance result based on the updated phenotypic impact predictions of the updated evidence models using one or more performance metrics.

In some aspects, variant interpretation support system 110 can evaluate the validation performance data and test performance data of the evidence model according to one or more performance metrics (e.g., diagnostic, classification, regression accuracy, etc.), which can consider both the accuracy (e.g., quality) of predictions as well as the coverage (e.g., quantity) of the possible molecular variants in a functional element (or molecule) of interest. For example, in some aspects, variant interpretation support system 110 can evaluate one or more performance metrics relating to diagnostic accuracy for one or more predictions of an evidence data 114. As would be appreciated by a person of ordinary skill in the art, various performance metrics can be used. For example, diagnostic metrics can include but are not limited to one or more of the following:

- (Raw) Accuracy: the proportion of true results among the total number of cases examined.
- Balanced Accuracy: a measure of true and false positives and negatives in binary classification which can be used when binary class representation is unbalanced (are of markedly different sizes), such as the Matthew's Correlation Coefficient
- True Positive Rate (TPR): measures the proportion of subjects having the characteristic or condition that are correctly identified as such.
- True Negative Rate (TNR): measures the proportion of subjects not having the characteristic or condition that are correctly identified as such.
- Positive Predictive Value (PPV): represents the probability of having the characteristic or condition among those that test positive.
- Negative Predictive Value (NPV): represents the probability of not having the characteristic or condition among those that test negative.
- True Positive (TP): a test result that detects the condition when the condition is present.
- True Negative (TN): a test result that does not detect the condition when the condition is absent.
- False Positive (FP): a test result that detects the condition when the condition is absent.
- False Negative (FN): a test result that does not detect the condition when the condition is present.
- Coverage (CVG): Fraction of the possible molecular variants in a functional element (or molecule) of interest.

In some aspects, evaluating evidence models using uniform sets of performance metrics on disjoint sets of molecular variants (e.g., validation performance data and test performance data) can overcome the problem of being unable to effectively compare the predictive performance of evidence models. As would be appreciated by a person of ordinary skill in the art, various performance metrics can be used, as well as distinct (e.g., uniform and non-uniform) disjoint sets of molecular variants. Existing variant interpretation support systems can be unable to assess the predictive performance of an evidence model because the diagnostic metric used to measure the performance of the evidence model varied across the diverse array of genes and disorders in clinical genetic testing. In addition, existing variant interpretation support systems are unable assess the predictive performance of an evidence model because the requested diagnostic metric of interest used during selection differed from the diagnostic metric of interest used by the creator of the evidence model during evaluation. Thus, because variant interpretation support system 110 evaluates the validation performance data and test performance data for an evidence model (or associated evidence data 114) using one or more performance metrics that are consistent across the molecular variants having known phenotypic impacts for a query set of functional elements, phenotypes, and contexts, variant interpretation support system 110 can provide objective and easily comparable validation performance data and test performance data for the evidence models, and associated evidence data 114, at any given time, unlike existing variant interpretation support systems used by clinical genetic testing providers.

In some aspects, variant interpretation support system 110 can generate an evidence model, or associated evidence data 114, according to a machine learning model. A machine learning model can be a program with tunable parameters that can be adjusted in response to previously received data in order to improve the predicting behavior of the model. In some other aspects, the variant interpretation support system 110 acquires an evidence model, or evidence data 114, from an external source (e.g., a public database containing predictions of phenotypic impacts of molecular variants as generated from a published computational predictor).

In some aspects, variant interpretation support system 110 can generate an evidence model using various input data 112 (e.g., clinical, functional, biochemical, biophysical, evolutionary, genetic, and other data as would be appreciated by a person of ordinary skill in the art). For example, variant interpretation support system 110 can apply unsupervised, semi-supervised, and supervised machine learning techniques (or combinations thereof) to generate (e.g., train) an evidence model—associated evidence data 114—such as a computational predictor, that associates raw and/or processed input data 112 of variant, residue, or molecular features with the raw and/or processed input data 112 of labeled phenotypic impacts (e.g., the pathogenicity or neutrality of genetic variants of known clinical significance), as can be determined from phenotypic impact knowledge base 102. Variant interpretation support system 110 can train one or more machine learning models to generate an evidence model in order to learn a series of general rules that predicts the phenotypic impacts (e.g., labels) of molecular variants (e.g., the phenotypic impacts) on the basis of the characteristics of variants, residues, or molecules (e.g., features) of the molecular variants. Variant interpretation support system 110 can determine these general rules by tuning the parameters of one or more machine learning models. As would be appreciated by a person of ordinary skill in the art, evidence model can represent one or more generated or imported evidence models.

In some aspects, variant interpretation support system 110 can retrain (or update) the machine learning model of an evidence model, such as a computational predictor or mutational hotspot, based on its associated evaluation data 116, such as its raw or processed validation performance data or test performance data. As would be appreciated by a person of ordinary skill in the art, variant interpretation support system 110 can iterate through training-evaluation strategies or processes until the evidence model, for example the computational predictor, achieves a threshold level of performance in its validation performance data, test performance data, or both. As would be appreciated by a person of ordinary skill in the art, variant interpretation support system 110 can specify the threshold levels of performance based on a multiplicity of factors, including one or more thresholds for one or more performance metrics (e.g., diagnostic, classification, regression accuracy, etc.).

In some aspects, variant interpretation support system 110 regularly incorporates (e.g., generates or imports), updates, evaluates, and validates evidence models, such as computational predictors. These new evidence models can be based on and generated in response to new data regarding the phenotypic impacts of molecular variants data received by variant interpretation support system 110.

After calculating and incorporating validation performance data or test performance data for evidence models in the evaluation database, variant interpretation support system 110 can rank the evidence model, or associated evidence data 114, among other the evidence models (or evidence data 114) based on its validation performance data, test performance data, (e.g., historical or simulated) track record of validation performance data, (e.g., historical or simulated) track record of test performance data, or combinations thereof. As would be appreciated by a person of ordinary skill in the art, variant interpretation support system 110 can rank the evidence model, or associated evidence data 114, on the basis of one or more performance metrics.

In some aspects, variant interpretation support system 110 can incorporate (e.g., generate or import), monitor, update, validate, select, distribute, and audit an evidence model, or its associated supporting data 118. As would be appreciate by a person of ordinary skill in the art, in some aspects, the variant interpretation support system 110 can perform the same (or related) procedures for incorporating (e.g., generating or importing), monitoring, updating, validating, selecting, distributing and auditing with respect to diverse classes of evidence models (e.g., mutational hotspots, computational predictors, or functional assays). Variant interpretation support system 110 can regularly generate or import new evidence models, or associated evidence data 114, for given molecular variants, functional elements (or molecules), phenotypes, contexts, and performance metrics of interest. Variant interpretation support system 110 can record and monitor the performance of an evidence model, or its associated supporting data 118. Variant interpretation support system 110 can update evidence models in response to new input data 112 or evaluation data 116. variant interpretation support system 110 can also validate an evidence model in response to receiving (e.g., new) disjoint data for molecular variants from phenotypic impact knowledge base 102. Variant interpretation support system 110 can select support from evidence models meeting specific performance requirements on the basis of validation performance data or test performance data or combinations thereof. Variant interpretation support system 110 can distribute predictions of the phenotypic impacts of molecular variants from selected evidence models, such as evidence data 114, in response to a query from variant interpretation terminal 138. Finally, variant interpretation support system 110 can enable auditing the availability, date of creation, or contents of supporting data 118—including input data 112 (e.g., labeled data used in training), evidence data 114 (e.g., evidence model predictions of phenotypic impacts), or evaluation data 116—from selected evidence models in response to an audit request from a variant interpretation terminal 138. As such, the variant interpretation support system 110 can both distribute and audit variant interpretation supporting data 118 provided by an evidence model and relating to the phenotypic impacts of molecular variants for one or more functional elements (or molecules), phenotypes, contexts, or set of variants of interest at a given time, in response to a queries and requests from a variant interpretation terminal 138.

In response to user input or automated requests, a variant interpretation terminal 138 can query variant interpretation support system 110 for the variant interpretation support from evidence models, and associated evidence data 114, that meet desired performance requirements for a given molecular variant—such as a genotypic (sequence) variant defined by chromosome, position, reference nucleotide, and mutation, or allele in a reference genome—for a given phenotype or set of phenotypes of interest and for a given diagnostic optimization strategy (e.g., that prioritizes true positive rate above balanced accuracy). In some aspects, variant interpretation support system 110 receives queries from a variant interpretation terminal 138 requesting variant interpretation support for one or more molecular variants. In some aspects, queries from a variant interpretation terminal 138 can delineate the functional elements, phenotypes, context, or performance metrics of interest. In some aspects, queries from a variant interpretation terminal 138 can delineate the performance requirements for the variant interpretation support. In some aspects, variant interpretation support system 110 responds with the corresponding phenotypic impact predictions for the highest-ranked evidence data 114 from the set of evidence models for a given molecular variant, functional element (or molecule), phenotype or set of phenotypes, and performance metrics of interest, along with metadata for auditing said evidence models and their associated supporting data 118. In some aspects, the evidence models have been ranked and selected on the basis of specific evaluation data 116 (e.g., validation performance data or test performance data), or a combination thereof. In some aspects, variant interpretation support system 110 can provide associated input data 112 (e.g., production data or test data), evidence data 114 (e.g., associated phenotypic impact predictions), evaluation data 116 (e.g., validation performance data or test performance data), and auditing information—including an audit record 128 and/or timestamp—to validate the availability, date of creation, and contents of input data 112, evidence data 114, or evaluation data 116 for the selected evidence models. As would be appreciated by a person of ordinary skill in the art, a portion or all of these various data items can be provided.

In some aspects, the auditing information can include a reference to the distributed database 126 containing the audit records 28, along with all associated audit record identifiers. For example, the auditing information can include a reference to a blockchain data structure containing the audit records 28.

In some aspects, variant interpretation support system 110 can communicate with variant interpretation terminal 138 over a network 136. Network 136 can be any network or combination of networks including the Internet, a local area network (LAN), a wide area network (WAN), a wireless network, a cellular network, or various other types of networks as would be appreciated by a person of ordinary skill in the art. For example, variant interpretation terminal 138 can be a remote terminal that queries variant interpretation support system 110 over network 136 for the most accurate evidence model, or associated evidence data 114, for a given molecular variant, functional element (or molecule), phenotype, or context. While the aspect of a remote terminal will be used throughout for illustration and explanation, variant interpretation terminal 138 need not be remote from variant interpretation support system 110, but can instead be local to the variant interpretation support system 110, such that variant interpretation terminal 138 communicates directly with variant interpretation system 110.

In some aspects, an auditor can obtain proof of the entry date and time of the (e.g., raw or processed) supporting data 118 for each evidence model, including input data 112, evidence data 114, evaluation data 116. For example, an auditor can query the distributed database 126 (e.g., the blockchain data structure) with the audit record identifiers (e.g., a blockchain receipt) corresponding to data related to an evidence model. In response, the auditor can receive a confirmation that a particular hash value 124 corresponding to supporting data 118 for auditing and audit record 128 of interest was available at a certain date and time.

This enables the auditor to determine (1) that an evidence model was incorporated (e.g., generated) using data available at the time of entry of its audit record 128 and (2) that the phenotypic impact predictions generated by an evidence model, or associated evidence data 114, were available at a certain date and time.

In response to user input or an automated request, variant interpretation terminal 138 can audit an evidence model, or its associated supporting data 118, in order to ensure any one or a combination of the following: (a) that the evidence model or associated supporting data 118 was available at a certain date and time, (b) that the evidence model or associated evidence data 114 was generated (e.g., trained) using specific input data 112 that was available at the date and time of evidence model creation, (c) that the evidence model or associated evidence data 114 was generated (e.g., trained) without the use of specific input data 112 that was not available at the date and time of evidence model creation, (d) that the evidence model or associated evidence data 114 contains specific phenotypic impact predictions (which can have been provided to the variant interpretation terminal 138), or (e) that the evidence model or associated evidence data 114 achieves the performance expected on the basis of validation performance data or test performance data reported in the evaluation data 116 on disjoint sets of data. This can provide confidence to variant interpretation terminal 138 that the provided variant interpretation support is based on evidence models, or associated evidence data 114, meeting the specified performance requirements and that the evidence model, or associated evidence data 114, has not been manipulated. This auditing can also provide patients and physicians additional confidence that their clinical genetic results were determined using robust and transparent evidence models and supporting data 118.

In some aspects, variant interpretation terminal 138 can obtain proof of the availability, content, and creation date and time, of supporting data 118—including input data 112, evidence data 114, evaluation data 116—used to generate a given evidence model (e.g., a computational predictor) or set of evidence models (e.g., a combination of computational predictors, mutational hotspots, and functional assays), which can then be provided to a user. For example, an auditor can instruct the variant interpretation terminal 138 to audit a computational predictor in the distributed database 126 (e.g., the blockchain) with the audit record 128 identifiers for supporting data 118 associated with the computational predictor of interest. In response, variant interpretation terminal 138 can receive a certificate of validation from the distributed database 126, including the hash value 124 of the supporting data 118. In some aspects, the certificate of validation can be a certificate of receipt provided from a third-party or data maintained by variant interpretation support system 110. For example, in some aspects, the certificate of validation can be a certificate of receipt provided from a blockchain data structure containing the hash value 124, date and time of creation of the entry associated with the audit record 128 of the supporting data 118. Variant interpretation terminal 138 can confirm that the certificate of validation matches the supporting data 118 for the computational predictor under audit by confirming that the validation code (e.g., computed hash value) corresponds to (1) the hash value 124 from the hash record 120 of a specific supporting data 118 (e.g., the evidence data 114 corresponding the predictions of phenotypic impacts for an individual computational predictor), (2) the hash value 124 from the hash records 120 of a single compressed object of supporting data 118 (for bulk database entries), or (3) the hash value 124 from the hash records 120 of a set of supporting data 118 (e.g., for bulk database entries).

Figure 2:
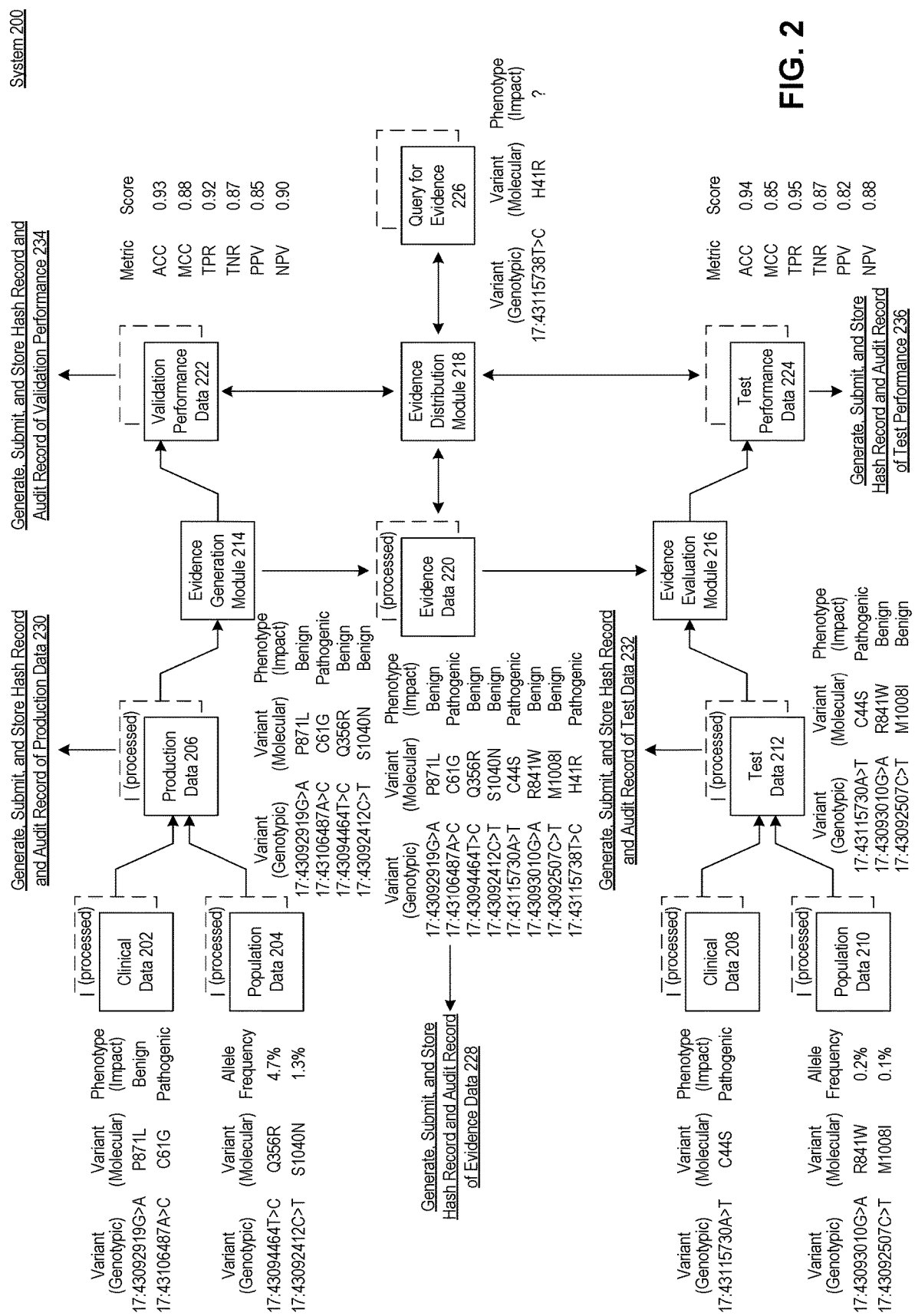
FIG. 2 is an example diagram of a system providing an optimal set of evidence models for describing or predicting the phenotypic impacts of molecular variants for one or more functional elements (or molecules), phenotypes, contexts, or set of variants of interest at a given time, according to some aspects.

FIG. 2 is an example diagram of system 200 for providing the objectively highest-performance evidence model for a protein-coding gene and phenotype, according to some aspects. FIG. 2 is discussed with reference to FIG. 1. In FIG. 2, production data 206 can represent a set of molecular variants with associated phenotypic impacts (e.g., molecular effects), as derived from diverse input data 112, such as clinical data 202 and population data 204. In FIG. 2, test data 212 can represent a set of molecular variants with associated phenotypic impacts (e.g., molecular effects), as derived from novel input data 112, such as clinical data 208 and population data 210, for variants that are disjoint from those contained in production data 206. As an example, the phenotypic impacts indicating whether the associated molecular variants in a given protein-coding gene are considered pathogenic or benign (e.g., neutral) in specific clinical condition.

In some aspects, after generating or importing production data 206, variant interpretation support system 110 utilizes an evidence generation module 214 to generate evidence data 220 from an evidence model, such as a computational predictor, and calculate the associated validation performance data 222 of the model using production data 206 for a given protein-coding gene and phenotype. For example, in the evidence data 220 generated by evidence generation module 214, the molecular variant H41R (e.g., genotypic (sequence) variant 17:43115738T>C) is predicted to belong to the class Pathogenic, with a probability of being classified as Pathogenic equal to P (Pathogenic) as estimated across the set of cross-validation folds (training/validation iterations) in which the molecular variant H41R were excluded in training. Variant interpretation support system 110 can adjust the parameters of the evidence model generating the evidence data 220.

In some aspects, variant interpretation support system 110 can evaluate the validation performance data 222 of the evidence model of evidence data 220. As would be appreciated by a person of ordinary skill in the art, evidence data 220 can be generated by a diversity of evidence models, including computational predictors, and can be generated using a diverse array of techniques and methods, including unsupervised, semisupervised, or supervised machine learning techniques and methods. As would be appreciated by a person of ordinary skill in the art, an evidence model can represent one or more (an ensemble of) evidence models generated using the production data 206.

In FIG. 2, variant interpretation support system 110 can utilize an evidence generation module 214 that determines the validation performance data 222 of the evidence model underlying evidence data 220, using a cross-validation scheme, such as a leave-one-out cross-validation (LOOCV) training and validation scheme. For example, in FIG. 2 summary statistics of the diagnostic performance metrics across the complete cross-validation scheme are aggregated and provided in the validation performance data 222. This recording process establishes a baseline of performance for evidence data 220.

In FIG. 2, variant interpretation support system 110 can utilize an evidence evaluation module 216 that determines the test performance data 224 of the evidence data 220 on the basis of test data 212.

In some aspects, variant interpretation support system 110 can leverage one or a combination of evidence generation modules 214 and evidence evaluation modules 216 to generate and evaluate a plurality of evidence models utilizing the production data 206 (e.g., training multiple computational predictors and mutational hotspots).

In some aspects, the variant interpretation support system 110 will generate, submit, and store hash records 120 and audit records 128 of production data 206, test data 212, evidence data 220, validation performance data 222, and/or test performance data 224 associated with an evidence model (e.g., steps 228, 230, 232, 234 and/or 236, respectively).

In some aspects, variant interpretation support system 110 can generate, submit, and store hash records 120 of the production data 206, test data 212, evidence data 220, validation performance data 222, and/or test performance data 224 by following a process of computing the hash value 124 of the corresponding data and storing a corresponding hash record 120 in a hash database 122, as shown in FIG. 1.

In some aspects, variant interpretation support system 110 can generate, submit, and store audit records 128 of the production data 206, test data 212, evidence data 220, validation performance data 222, and/or test performance data 224 by following a process of accessing the hash value 124 of the corresponding data in the hash record 120 of a hash database 122, entering it in a distributed database 126 and storing the associated audit record 128 of the entry in an audit database 130 shown in FIG. 1. The audit record 128 can include a timestamp representing when the corresponding data was established and a record identifier that uniquely identifies the entry in the distributed database 126.

In some aspects, variant interpretation support system 110 can compute a target hash value from a target subset data from one or more supporting data 118, such as the phenotypic impact of an individual molecular variant as predicted by an evidence model, a granular form of evidence data 220. In some aspects, variant interpretation support system 110 can record the target hash value (e.g., computed from target subset data) into a target hash record in the hash database. In some aspects, the target hash record includes additional hash value information, including for example, a master hash value that can be recomputed from (or used to validate) the target hash records of a plurality of target subset data. For example, in some aspects, variant interpretation support system 110 can compute the master hash value as the root of a set of target hash values (e.g., leaves) using a Merkle tree structure. Together with systems, methods and applications described and enabled herein, this recordation process can ensure that there is an effective, objective way to audit the availability, date of creation, and content of a plurality of granular forms of supporting data 118 associated with a single audit record 128 derived from a master hash value.

In some aspects, variant interpretation support system 110 can rank evidence data 220 among other evidence data describing the phenotypic impacts of molecular variants for one or more functional elements (or molecules), phenotypes, contexts, or set of variants of interest at a given time. For example, variant interpretation support system 110 can rank evidence data 220 from computational predictor among other evidence models (e.g., computational predictors and functional assays) based on its validation performance data 222 or test performance data 224. As would be appreciated by a person of ordinary skill in the art, validation performance data 222 or test performance data 224 for evidence data 220 can be compared to other performance results on the basis of one or more performance metrics of interest. Using multiple performance metrics can enable evidence models to be ranked under diverse heuristics, optimized to the clinical context of interest. As would be appreciated by a person of ordinary skill in the art, the clinical context of interest can require optimization of diagnostic strategies with regards to specific performance metrics.

In some aspects, in order to determine the accuracy of an evidence model, the variant interpretation support system 110 validates evidence model performance using one or more sets of validation performance data 222, one or more sets of test performance data 224, or combinations of validation performance data 222 and test performance data 224. For example, variant interpretation support system 110 can validate the performance of evidence data 220 by confirming the test performance data 224 falls within a specific confidence interval (or range of dispersion) for one or more performance metrics as estimated on the basis of validation performance data 222, or previous test performance data. As would be appreciated by a person of ordinary skill in the art, various model validation techniques can be used to validate the conformance of test performance data 224 with respect to validation performance data 222, or previous test performance data 224.

For example, in FIG. 2, variant C44S is a molecular variant discovered to be pathogenic (and annotated as such in the clinical data 208) at a time after the creation of evidence data 220. While this variant was not in the production data 206 for evidence data 220, evidence data 220 accurately predicts its phenotypic impact to be pathogenic.

In some aspects, after calculating the validation performance data 222 and/or test performance data 224, variant interpretation support system 110 can rank evidence model 220 based on its validation performance data 222 and/or test performance data 224, or a combination thereof.

In a query for evidence 226, variant interpretation terminal 138 can request an optimal set of evidence data 220 for describing or predicting the phenotypic impacts of molecular variants for one or more functional elements (or molecules), phenotypes, contexts, or set of variants of interest at a given time. For example, the query can request the production data 206, validation performance data 222, test performance data 224, and the predicted phenotypic impact for evidence data 220 with the highest balanced accuracy as measured by the Matthew's Correlation Coefficient (MCC) in test performance data 224 for a molecular variant under consideration for a specific phenotype of interest. In response, handling queries through an evidence distribution model 218, variant interpretation support system 110 can return the requested supporting data 118 (e.g., production data 206, validation performance data 222, test performance data 224, and the phenotypic impact prediction) for the evidence data 220 with the highest balanced accuracy for the molecular variant and phenotype under consideration. The query can also include the target performance metrics of interest for optimization. In this case, variant interpretation support system 110 can return the most accurate evidence model for the particular diagnostic metric(s) of interest.

In some aspects, the evidence distribution module 218 of the variant interpretation support system 110 can include hash records 120 and audit records 128 for the requested supporting data 118 to confirm the content, availability, or date of creation of the provided supporting data 118. In some aspects, the evidence distribution module 218 can access information in the hash database 122 to identify the hash records 120 of the provided supporting data 118, and uses the hash value 124 of the hash records 120 to recover the audit records 128 of the associated supporting data 118. In some aspects, to enable the auditing of the provided supporting data 118, the evidence distribution module 218 returns the query records 132 with the desired supporting data 118, the associated hash records 120 (e.g., including the hash value 124 and hash function), and the associated audit records 128.

In some aspects, variant interpretation terminal 138 can apply these methods to obtain proof of the availability, content, and creation date and time, of supporting data 118. For example, an auditor can instruct variant interpretation terminal 138 to audit the evidence data 220 associated with the phenotypic impacts provided in response to a query. Using the audit record 128 of the evidence data 220 in the response, the variant interpretation terminal can certify the entry in the distributed database 126 (e.g., the blockchain) by receiving a certificate of validation from the database, including the hash value 124 stored in distributed database 126. In some aspects, the certificate of validation can be a certificate of receipt provided from a third-party or data maintained by variant interpretation support system 110. For example, in some aspects, the certificate of validation can be a certificate of receipt provided from a blockchain data structure containing the hash value 124, date and time of creation for the entry associated with the audit record 128 of the supporting data 118. Variant interpretation terminal 138 can confirm that the certificate of validation matches the supporting data 118 for the evidence model under audit by confirming that the validation code (e.g., computed hash value) corresponds to the (1) the hash value 124 from the hash record 120 of a specific supporting data 118 (e.g., the evidence data 220 corresponding to the predictions of phenotypic impacts for an individual computational predictor), (2) the hash value 124 from the hash records of a single compressed object of supporting data 118 (for bulk database entries), or (3) the hash value 124 from the hash records 120 of a set of supporting data 118 (e.g., for bulk database entries).

Figure 3:
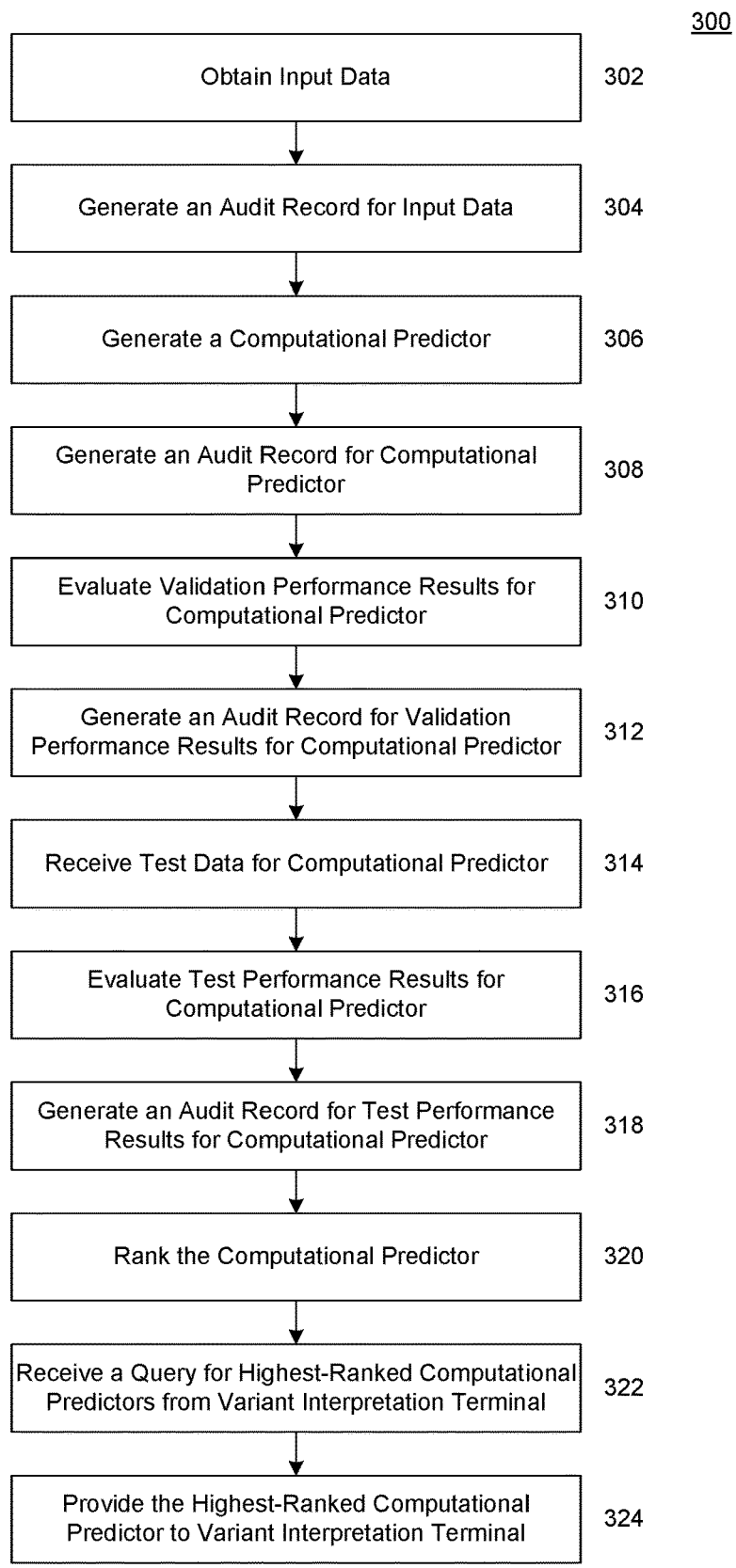
FIG. 3 is a flowchart illustrating a process providing an optimal set of evidence models for describing or predicting the phenotypic impacts of molecular variants for one or more functional elements (or molecules), phenotypes, contexts, or set of variants of interest at a given time, according to some aspects.

FIG. 3 is a flowchart for a method 300 for providing an optimal set of evidence models for describing or predicting the phenotypic impacts of molecular variants for one or more functional elements (or molecules), phenotypes, contexts, or set of variants of interest at a given time, according to one aspect. Method 300 can be performed by processing logic having hardware (e.g., circuitry, dedicated logic, programmable logic, microcode, etc.), software (e.g., instructions executing on a processing device), or a combination thereof. It is to be appreciated that not all steps can be needed to perform the disclosure provided herein. Further, some of the steps can be performed simultaneously, or in a different order than shown in FIG. 3, as will be understood by a person of ordinary skill in the art.

Method 300 shall be described with reference to FIG. 1 and FIG. 2. However, method 300 is not limited to said example aspects.

In 302, variant interpretation support system 110 receives input data 112, including clinical data 202 and population data 204, enabling the generation (or import) of an evidence model. In some aspects, variant interpretation support system 110 derives phenotypic impacts (e.g., labels) described in production data 206 from clinical data 202 and population data 204.

In 304, variant interpretation support system 110 generates, submits, and stores hash records 120 and audit records 128 for production data 206. As would be appreciated by a person of ordinary skill in the art, variant interpretation support system 110 can generate or acquire a plurality of input data 112, including data from a diverse set of knowledge bases (102, 104, 106, 108), and similarly generate, submit, and store hash records 120 and audit records 128 for this data.

In 306, variant interpretation support system 110 generates (e.g., trains) a computational predictor (e.g., evidence model) using the phenotypic impacts (e.g., labels) of molecular variants as described in production data 206.

In 308, variant interpretation support system 110 generates, submits, and stores hash records 120 and audit records 128 for evidence data 220 generated by the computational predictor (e.g., evidence model).

In 310, variant interpretation support system 110 evaluates the validation performance data 222 of the computational predictor (e.g., evidence model) as computed using a leave-one-out cross-validation training/validation scheme. As would be appreciated by a person of ordinary skills in the art, a plurality of validation schemes and techniques in the fields of machine learning and data science can be used to derive the validation performance data 222 of computational predictors trained on production data 206.

In 312, variant interpretation support system 110 generates, submits, and stores hash records 120 and audit records 128 for validation performance data 222.

In 314, variant interpretation support system 110 receives new input data 112 (e.g., clinical data 208 and population data 210) and generates test data 212 describing the phenotypic impacts of molecular variants not included in production data 206.

In 316, variant interpretation support system 110 evaluates test performance data 224 of the computational predictor (e.g., evidence model) as computed on the basis of the disjoint set of molecular variants described in test data 212.

In 318, variant interpretation support system 110 generates, submits, and stores hash records 120 and audit records 128 for test performance data 224.

In 320, variant interpretation support system 110 filters, ranks, and/or selects an optimal set of evidence models, including, for example, the computational predictor from step 306, on the basis of its validation performance data 222 and test performance data 224, ranking and selecting the computational predictor (from step 306) as the computational predictor with a balanced accuracy (e.g., Matthew's Correlation Coefficient (MCC)) in the test performance data 224 within the expected range (e.g., 95% confidence interval) of the balanced accuracy estimates of the validation performance data 222, and the highest balanced accuracy (MCC). In this example, variant interpretation support system 110 can limit the selection of evidence models (or associated evidence data 114) to those in which test performance data falls within expected range from the validation performance data 222, and subsequently selects the evidence model (or associated evidence data 114) with the objectively highest performance. As would be appreciated by a person of ordinary skill in the art, the optimal set of evidence models can include a single evidence model or multiple evidence models.

In 322, variant interpretation support system 110 receives a query from variant interpretation terminal 138 for the predicted phenotypic impact of a specific molecular variant of interest that maximizes the balanced accuracy (MCC) of the interpretation.

In 324, variant interpretation support system 110 responds with the predicted phenotypic impact from the computational predictor (from step 306).

Figure 4:
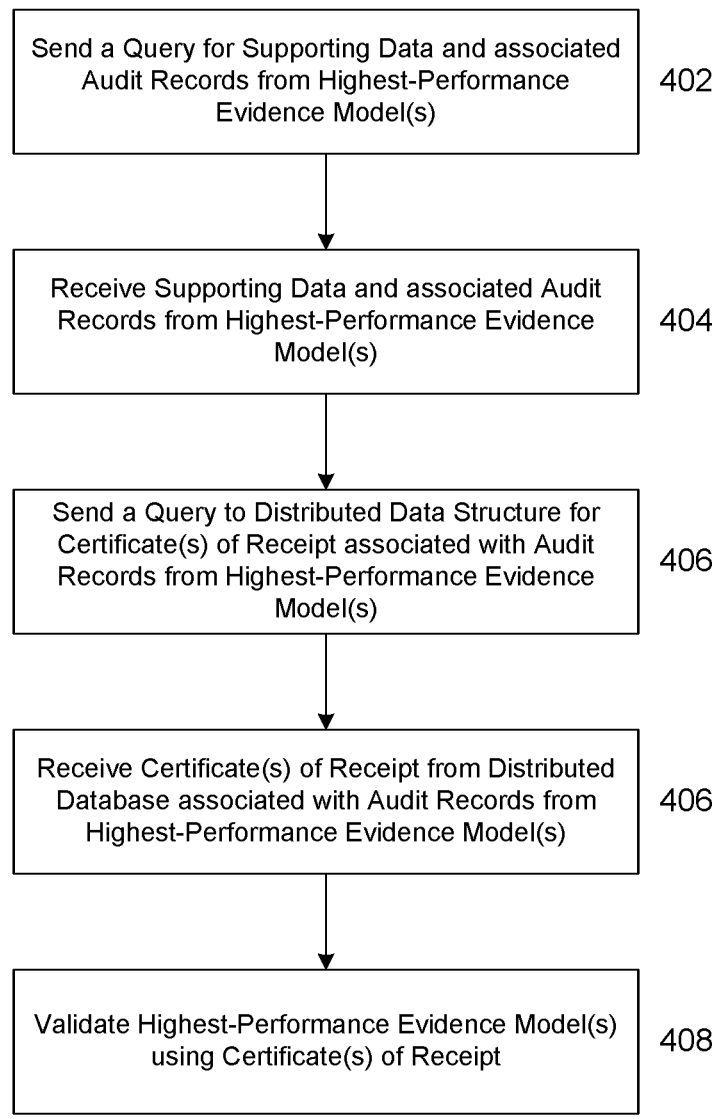
FIG. 4 is a flowchart illustrating a process for auditing an evidence model for describing or predicting the phenotypic impacts of molecular variants for one or more functional elements (or molecules), phenotypes, contexts, or set of variants of interest at a given time, according to some aspects.

FIG. 4 is a flowchart for a method 400 for auditing a computational predictor for a given molecular variant, functional element (or molecule), phenotype, or context, according to an aspect. Method 400 can be performed by processing logic having hardware (e.g., circuitry, dedicated logic, programmable logic, microcode, etc.), software (e.g., instructions executing on a processing device), or a combination thereof. It is to be appreciated that not all steps can be needed to perform the disclosure provided herein. Further, some of the steps can be performed simultaneously, or in a different order than shown in FIG. 4, as will be understood by a person of ordinary skill in the art.

Method 400 shall be described with reference to FIG. 1 and FIG. 2. However, method 400 is not limited to said example aspects.

In 402, variant interpretation terminal 138 sends a query to variant interpretation support system 110 for the evidence model with the highest balance accuracy (MCC) for a functional element and phenotype of clinical interest. In some aspects, the query is also for a specific context of interest.

In 404, variant interpretation terminal 138 receives supporting data 118 from the evidence model whose evidence data 220 displays the highest test performance data 224 balanced accuracy (e.g., MCC) and whose test performance data 224 balanced accuracy is within the expected range (e.g., 95% confidence interval) of the balanced accuracy estimates of the evidence model's corresponding validation performance data 222, among evidence models for the functional element and phenotype of interest. Variant interpretation terminal 138 further receives audit records 128 associated with the provided supporting data 118 for the functional element and clinical phenotype of interest. The supporting data 118 can include the production data 206, the clinical data 202, the clinical data 204, the validation performance data 222, the test performance data 224, and the evidence data 220.

In 406, variant interpretation terminal 138 sends a query to the distributed database 126 that contains the received audit records 128 and receives a certificate of validation for the audit record 128 of each supporting data 118 from the distributed database 126. The certificate of validation can include hash value 124 and the timestamp from the corresponding audit record 128 in the distributed database 126. As would be appreciated by a person of ordinary skill in the art, the certificate of validation can be certificate of receipt provided by a third-party or can be data maintained by variant interpretation support system 110.

In 408, variant interpretation terminal 138 confirms that the provided supporting data 118 matches the audit record 128 by evaluating the equivalence of the validation code (e.g., computed hash value of the supporting data 118) and the hash value 124 of the audit records 128 associated with supporting data 118. Matching the validation code and the hash value 124 confirms the provided supporting data 118 was generated at or before the timestamp provided in step 406. For example, matching the validation code computed from evidence data 220 provided as supporting data 118 in the query and the hash value 124 of the evidence data 220 can allow an auditing variant interpretation terminal 138 to confirm the specific predicted phenotypic impacts provided by evidence data 220 were generated on or before the timestamp of the audit record 128. For example, variant interpretation terminal 138 can compare the timestamp in step 406 to a timestamp of interest to verify that evidence data 220 was generated before a timestamp of interest. Variant interpretation terminal 138 can further compare the hash value 124 in step 406 to the validation code derived from the production data 206 to determine that the evidence data 220 was generated using the provided production data 206.

Figure 5:
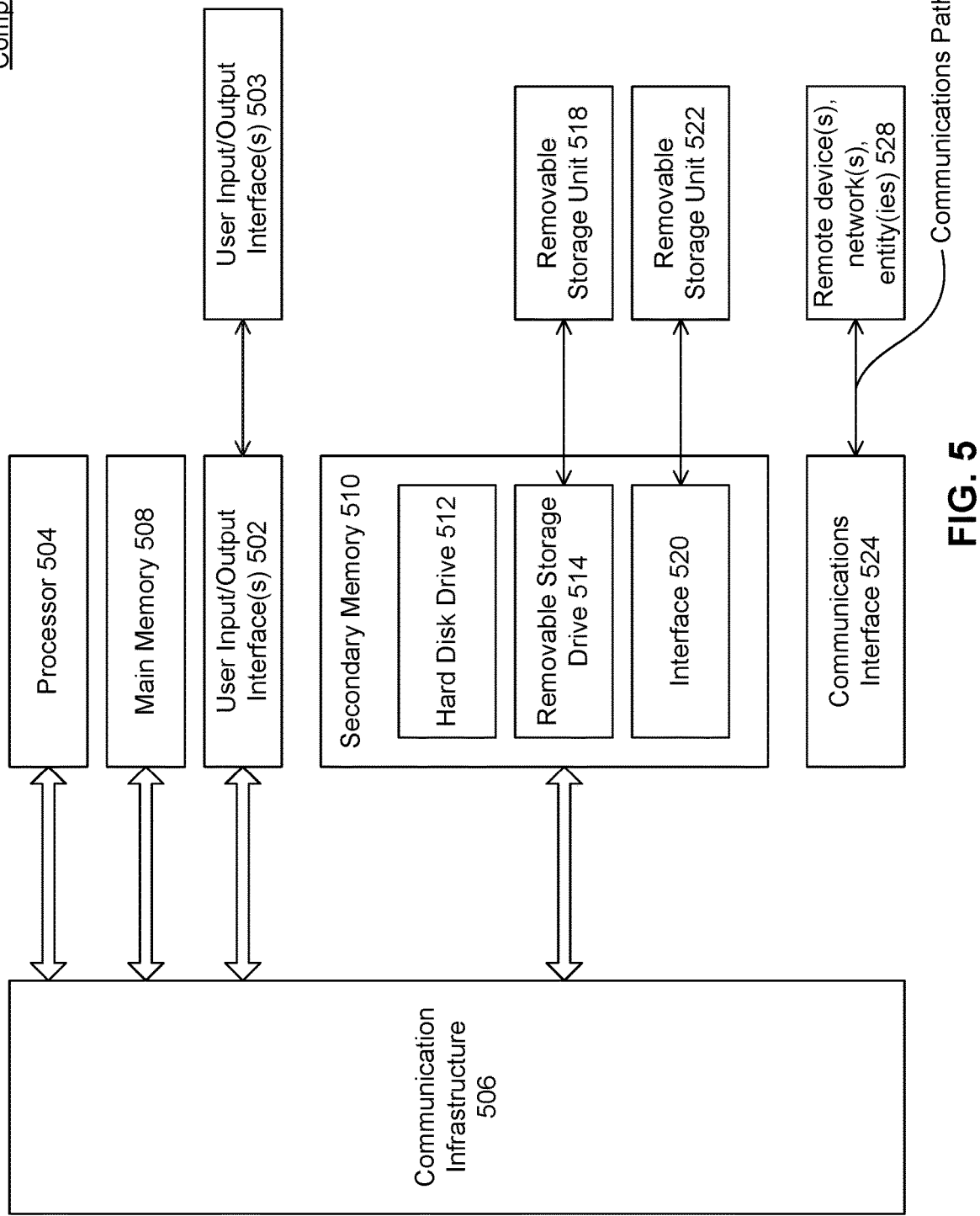
FIG. 5 is an example computer system useful for implementing various aspects of the inventions described herein.

Various aspects can be implemented, for example, using one or more computer systems, such as computer system 500 shown in FIG. 5. Computer system 500 can be used, for example, to implement method 300 of FIG. 3. For example, computer system 500 can generate a validation record for a trained computational predictor. Computer system 500 can further be used, for example, to implement method 400 of FIG. 4. For example, computer system 500 can provide the most accurate computational predictor to a user at a genetic testing provider, along with metadata associated with the most accurate computational predictor. Computer system 500 can further map a plurality of tones to a resource block based on the determined resource block allocation, according to some aspects. Computer system 500 can be any computer capable of performing the functions described herein.

Computer system 500 can be any well-known computer capable of performing the functions described herein.

Computer system 500 includes one or more processors (also called central processing units, or CPUs), such as a processor 504. Processor 504 is connected to a communication infrastructure or bus 506.

One or more processors 504 can each be a graphics processing unit (GPU). In an aspect, a GPU is a processor that is a specialized electronic circuit designed to process mathematically intensive applications. The GPU can have a parallel structure that is efficient for parallel processing of large blocks of data, such as mathematically intensive data common to computer graphics applications, images, videos, etc.

Computer system 500 also includes user input/output device(s) 503, such as monitors, keyboards, pointing devices, etc., that communicate with communication infrastructure 506 through user input/output interface(s) 502.

Computer system 500 also includes a main or primary memory 508, such as random access memory (RAM). Main memory 508 can include one or more levels of cache. Main memory 508 has stored therein control logic (i.e., computer software) and/or data.

Computer system 500 can also include one or more secondary storage devices or memory 510. Secondary memory 510 can include, for example, a hard disk drive 512 and/or a removable storage device or drive 514. Removable storage drive 514 can be a floppy disk drive, a magnetic tape drive, a compact disk drive, an optical storage device, tape backup device, and/or any other storage device/drive.

Removable storage drive 514 can interact with a removable storage unit 518.

Removable storage unit 518 includes a computer usable or readable storage device having stored thereon computer software (control logic) and/or data. Removable storage unit 518 can be a floppy disk, magnetic tape, compact disk, DVD, optical storage disk, and/any other computer data storage device. Removable storage drive 514 reads from and/or writes to removable storage unit 518 in a well-known manner.

According to an exemplary aspect, secondary memory 510 can include other means, instrumentalities or other approaches for allowing computer programs and/or other instructions and/or data to be accessed by computer system 500. Such means, instrumentalities or other approaches can include, for example, a removable storage unit 522 and an interface 520. Examples of the removable storage unit 522 and the interface 520 can include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 500 can further include a communication or network interface 524. Communication interface 524 enables computer system 500 to communicate and interact with any combination of remote devices, remote networks, remote entities, etc. (individually and collectively referenced by reference number 528). For example, communication interface 524 can allow computer system 500 to communicate with remote devices 528 over communications path 526, which can be wired and/or wireless, and which can include any combination of LANs, WANs, the Internet, etc. Control logic and/or data can be transmitted to and from computer system 500 via communication path 526.

In an aspect, a tangible apparatus or article of manufacture comprising a tangible computer useable or readable medium having control logic (software) stored thereon is also referred to herein as a computer program product or program storage device. This includes, but is not limited to, computer system 500, main memory 508, secondary memory 510, and removable storage units 518 and 522, as well as tangible articles of manufacture embodying any combination of the foregoing. Such control logic, when executed by one or more data processing devices (such as computer system 500), causes such data processing devices to operate as described herein.

Based on the teachings contained in this disclosure, it will be apparent to persons skilled in the relevant art(s) how to make and use aspects of this disclosure using data processing devices, computer systems and/or computer architectures other than that shown in FIG. 5. In particular, aspects can operate with software, hardware, and/or operating system implementations other than those described herein.

It is to be appreciated that the Detailed Description section, and not any other section, is intended to be used to interpret the claims. Other sections can set forth one or more but not all exemplary aspects as contemplated by the inventor(s), and thus, are not intended to limit this disclosure or the appended claims in any way.

While this disclosure describes exemplary aspects for exemplary fields and applications, it should be understood that the disclosure is not limited thereto. Other aspects and modifications thereto are possible, and are within the scope and spirit of this disclosure. For example, and without limiting the generality of this paragraph, aspects are not limited to the software, hardware, firmware, and/or entities illustrated in the figures and/or described herein. Further, aspects (whether or not explicitly described herein) have significant utility to fields and applications beyond the examples described herein.

Aspects have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative aspects can perform functional blocks, steps, operations, methods, etc. using orderings different than those described herein.

References herein to "one aspect," "an aspect," "an example aspect," or similar phrases, indicate that the aspect described can include a particular feature, structure, or characteristic, but every aspect can not necessarily include the particular feature, structure, or characteristic. Moreover, such phrases are not necessarily referring to the same aspect. Further, when a particular feature, structure, or characteristic is described in connection with an aspect, it would be within the knowledge of persons skilled in the relevant art(s) to incorporate such feature, structure, or characteristic into other aspects whether or not explicitly mentioned or described herein. Additionally, some aspects can be described using the expression "coupled" and "connected" along with their derivatives. These terms are not necessarily intended as synonyms for each other. For example, some aspects can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary aspects, but should be defined only in accordance with the following claims and their equivalents.

In some aspects, the methods used to generate Production Data 204 and Test Data 212, including the particular definition of truth sets describing the phenotypic impacts can be generated in a multitude of ways from one or multiple knowledge bases 102, 104, 106 and 108. In other aspects, multiple truth set definition can be defined from a variety of sources of clinical variant interpretations that vary in one or more properties, such as quality or scope or quality over time. In other aspects, a variety of truth set definitions can be necessary in some contexts to generate sufficient data before proceeding to generate evidence data. In other aspects, multiple appropriate methods for converting knowledge base data 102, 104, 106 and 108 into appropriate input data 112 can exist. For example, interpreting Population Knowledge Base 104 as a truth set can require one or more appropriate population frequency cutoffs based on the characteristics of the phenotype described by the truth set, such as penetrance, prevalence, age of onset or inheritance pattern.

In other aspects, the Validation Performance Data 222 can be evaluated using Production Data 206 derived from multiple methods. For example, Evidence Data 220 can be derived using Production Data 206 derived from inclusion of all Clinical Data 202, while the Validation Performance Data 222 can be derived by evaluating the Evidence Data 220 with Production Data 206 derived from a limited set of Clinical Data 202.

In some aspects, the particular method or methods associated with Evidence Data 202 used to generate Production Data 206 and Validation Data 222 can be distinct than the particular method or methods used to generate Test Data 212. In some aspects, the Test Performance Data 224 can take into account the methods used in Production Data 206 and Validation Data 222 to create a disjoint truth set devoid of knowledge included in zero, one or more methods used in Production Data 206. In other aspects, multiple methods used to generate Test Performance Data 224 can be used. For example, Test Performance Data 224 can generate two or more scores while varying the Clinical Data 202 used to generate Test Performance Data 224.

In some aspects, the particular methods used to generate Production Data 206 and Test Data 212 can be evaluated on the basis of multiple methods. In some aspects, the relative quality of methods used to generate Production Data 206 and Test Data 212 that is generated can be evaluated based on the self consistency of the methods over time. In other aspects, the relative quality of methods used to generate Production Data 206 can be assessed based on the Validation Performance Data 222 and Test Performance Data 224 of Evidence Data 220 generated from Production Data 206 stemming from each method. In other aspects, the relative ranking of methods used to generate Production Data 206 and Test Data 212 can change over time. In other aspects, the relative ranking of methods used to generate Production Data 206 and Test Data 212 can be determined across multiple Evidence Data 220.

In some aspects, Evidence Data 220 for a single phenotype are generated on the basis on one or more particular definitions of Production Data 206. Similarly, Validation Performance Data 222 for Evidence Data 220 can be evaluated against one or more definitions of Production Data 206. Similarly, Test Performance Data 224 for Evidence Data 220 can be evaluated against one or more definitions of Test Data 212. For example, the Test Performance Data 224 or Validation Performance Data 222 for Evidence Data 220 can be generated using all Clinical Data 208 and Clinical Data 202 respectively, or a subset of the Clinical Data most relevant for a particular phenotype.

In some aspects, Evidence Data 220 can be calibrated after being generated. In some aspects, Evidence Data 220 can be adjusted to maximize concordance with a different definition of Production Data 206, or an analogous version of Production Data 206 generated with Clinical Data 202 from a different date. In other aspects, multiple Evidence Data 220 can be grouped by virtue of being generated from the same or similar definition of Production Data 206 and calibrated together. For example, one or more Evidence Data 220 generated from a particular definition of Production Data 206 known to over-estimate the probabilities of Pathogenic phenotype can be calibrated with respect to a definition of Production Data 206 that is more concordant with real-world probabilities of a Pathogenic phenotype. In some aspects, calibration methods can apply a transformation to probabilities of pathogenicity within Evidence Data 220 to maintain the rank of probabilities while providing a better real-world probability of pathogenicity. In other aspects, calibration methods can determine an optimal probability cutoff above and below which molecular variants can be optimally classified per the particular performance requirements set forth. As can be appreciated by a person having ordinary skill in the art, a variety of calibration techniques can be used to optimize concordance between Evidence Data 220 and Production Data 206 or Test Data 212. In some aspects, calibration methods are implemented as part of Evidence Generation Module 214 or Evidence Evaluation Module 216. In other aspects, the particular parameters and methods of calibration methods are stored as part of Validation Data 222 and Test Performance Data 224.

As can be appreciated by a person skilled in the art, the particular balance or quality of data using to evaluate predictions can alter the measured performance of predictions. For example, the PPV and NPV performance of a diagnostic can vary dramatically depending on the distribution of true-positives and true-negatives in the testing population. In some aspects, Production Data 206 and Test Data 212 can be modified prior to calculating the Validation Performance Data 222 and Test Performance data 224, respectively, to achieve a particular result. In some aspects, the Validation Performance Data 222 and Test Performance Data 224 can be calculated after positive and negative cases are balanced. For example, a Production Data 206 with 100 variants and 10 Benign variants can be resampled to achieve an equal number of Benign and Pathogenic variants prior to the calculation of Validation Performance Data 222. In other aspects, the particular phenotype distributions from Production Data 206 or Test Data 212 can be resampled to achieve parity with the testing population defined in Query for Evidence 226. In other aspects, the Validation Data 222 and Test Performance Data 224 can be directly recalculated to represent a particular phenotype distribution. In other aspects, the Test Performance Data 224 might alter the distribution of Test Data 212 to achieve parity with a particular Production data 206. As can be appreciated by a person skilled in the art, modification of Validation Performance Data 222 and Test Performance Data 224 to alter the apparent distribution or quality of Production Data 206 and Test Data 212, respectively, can occur at time generating performance data, or in response to a particular Query for Evidence 226. In some aspects, by achieving parity between Validation Performance Data 222 and Test Performance Data 224 allows the Evidence Distributino Module 218 to more directly compare and rank the population-sensitive metrics, such as NPV and PPV.

In some aspects, Evidence Data 220 can be optimized to achieve particular performance metric in Validation Performance Data 222 or Test Performance Data 224 by restricting Evidence Data 220 to those variants with more confident predictions. For example, Evidence Data 220 can not achieve a particular performance metric threshold when all variants are considered, but can reach the same performance metric threshold if only the 80% most-confident predictions are considered. In some aspects, the optimization parameters and methods, such as the optimal confidence threshold, are stored with Validation Performance Data 222 and Test Performance Data 224.

In some aspects, the calibration and optimization parameters from Validation Performance Data 222 and Test Performance Data 224 are applied to predictions from Evidence Data 220 in the Evidence Distribution Module 218. In some emobdiments, the Evidence Distribution Module provides both the original Evidence Data 220 and the optimized Evidence Data 220 provided as Query for Evidence 226.

In some aspects, multiple calibration and optimization techniques for Validation Performance Data 222 and Test Performance Data 224 are generated to achieve specific performance requirements. The Evidence Distribution Module 218 will retrieve the particular calibration and optimization technique that best meet the requirements for the Query for Evidence 226.

In some aspects, multiple Evidence Data 220 meet the requirements for the Query for Evidence 226. In other aspects, multiple calibration or optimization techniques of Evidence Data 220 meet the requirements Query for Evidence 226. In these cases, the the Evidence Distribution Module 218 must choose one or more Evidence Data 220 from which to provide a response to the Query for Evidence 226. In some aspects, the available Evidence Data 220 are ranked-ordered by their available Validation Performance Data 222 and Test Performance Data 224 according to the performance requirements from the Query for Evidence 226. In other aspects, the Evidence Distribution Model 218 can rank-order Evidence Data 220 according to metrics which are not specific to any particular Evidence Data 220. In other embodiments, the Evidence Distribution Model 218 can combine two or more rank-ordered Evidence Data. For example, the Evidence Distribution Module 218 first order can rank-order Evidence Data 220 by a particular metric from Validation Performance Data 220, then ascending by the bulk performance of Evidence Data 220 generated from equivalent Production Data 206 across many Evidence Data 220.

In some aspects, after ranking Evidence Data 220 the Evidence Distribution Module 218 can not find an Evidence Data 220 sufficiently performant to meet the requirements of Query for Evidence 226. In some aspects, the Evidence Distribution Module 218 can not provide the highest-ranked Evidence Data 220. In some aspects, if the Query for Evidence 226 requests the highest-ranked model, the Evidence Distribution Module 218 can still provide the Evidence Data 220 even if it does not meet the requirements of the Query for Evidence 226. In some aspects, the Query for Evidence 226 can not have specific performance thresholds, but can request the Evidence Data 220 which achieves the highest rank according to a ranking defined by the Query for Evidence 226 and executed by the Evidence Distribution Module 218.

In some aspects, Evidence Data 220 can provide and be evaluated with respect to non-classification-based interpretation and validation techniques. For example, evidence Data 220 can predict phenotype classification (e.g Pathogenic or Benign), probabilities (e.g. 22% chance of pathogenicity), or higher-dimensional phenotypes. For example, Validation Performance Data 222 can store the non-classification-based metrics of Evidence Data 222 with respect to Production Data 206, such as Area-under-the-Receiver-Operator-Curve or Spearman Correlation Coefficient. In some aspects, the evidence Distribution Module 218 will rank appropriate Evidence Data 220 using non-classification-based metrics in isolation, or alongside other metrics. In other aspects, the Evidence Distribution Module 218 can provide continuous and classification-based scores from Evidence Data 220.

As can be appreciated in a person skilled in the art, some applications of the Variant Interpretation Support System can exist in the realm of ranking a list of variants in order of probability of one or multiple phenotypes. For example, some users of the Variant Interpretation Support System can be interested in identifying the most likely causal variant in a patient exhibiting a particular phenotype. In some aspects, the Query for Evidence 226 will request the relative phenotype probabilities of a list of variants. In these cases, the Evidence Distribution Module will rank and collect the most performant Evidence Data 220 for each variant in the Query for Evidence 206. In some aspects, the Evidence Distribution Module 218 will return a list of all variants above a particular probability of phenotype. In some aspects, the particular probability of phenotype is set forth internally. In other aspects, the particular probability of phenotype is set forth in accordance with the requirements set forth in the Query for Evidence 226. In other aspects, the Evidence Distribution Module 218 will provide the list of variants from the Query for Evidence in rank-order according to their relative probabilities for one or more phenotypes. In other aspects, the Evidence Distribution Module will include the relative probabilities associated with each phenotype from each variant in the Query for Evidence 226. In other aspects, only a certain number or percentage of the evidence in the Query for Evidence are returned by the Evidence Distribution Module.

In some aspects, the Variant Interpretation Support System can track the Query for Evidence 226 from particular querying entities in a distinct database. At a later point, the Variant Interpretation Support System can use the recorded Query for Evidence 226 as part of Input Data to further refine Production Data 206 or Test Data 212. For example, Clinical Data 208 can have been partially derived from a Query for Evidence 226 and Evidence Data 220, at which point the Variant Interpretation Support system can opt to exclude particular Clinical Data 208 to avoid tautological conclusions in the Test Performance Data 224.

Figure 6:
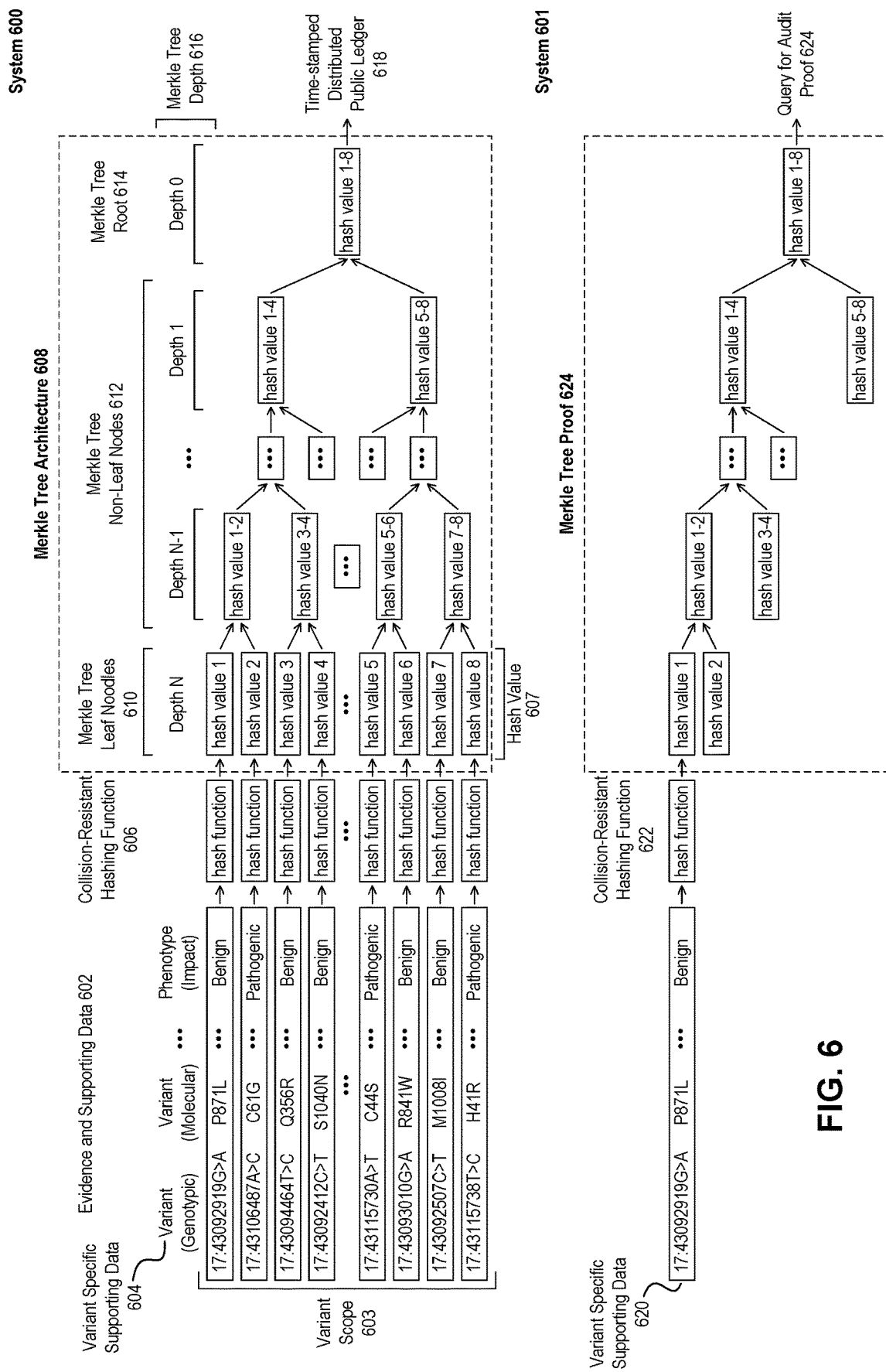
FIG. 6 is a figure for a system 600 for generating a Merkle tree from a list of evidence and supporting data entries and submitting it to a time-stamped public ledger, according to one aspect.

System 600 (FIG. 6) can be performed by processing logic having hardware (e.g., circuitry, dedicated logic, programmable logic, microcode, etc.), software (e.g., instructions executing on a processing device), or a combination thereof. It is to be appreciated that not all steps can be needed to perform the disclosure provided herein. Further, some of the steps can be performed simultaneously, or in a different order than shown in FIG. 6, as will be understood by a person of ordinary skill in the art Systems 600 and 601 shall be described with reference to FIG. 1 and FIG. 2. However, system 600 is not limited to said example aspects.

Evidence and supporting data 602 can be aggregated for a set of predictions from Evidence Data 220 and any supporting data, such as Production Data 206, Validation Performance Data 222, or any other Input Data 122. The supporting data for each variant can be separated into a Variant Specific Supporting Data 604 including identifying information (such as genotypic variant and molecular variant). In some aspects, Variant Specific Supporting Data 604 includes information specific to the Evidence Model 220 predictions or Validation Performance Data 222 specific to the variant. In other aspects, Variant Specific Supporting Data 604 includes information about the Input Data 122 or specific parameters from the Evidence Model 214. The Variant Specific Supporting Data 5604 can span a predefined Molecular Variant Scope 603, for example: all predictions for missense variants from a particular Evidence Data 220.

For each Variant Specific Supporting Data 604, a Collision-Resistant Hash Function 606 can be defined to deterministically convert the Variant Specific Supporting Data 604 into a hash value 607 for each Variant Specific Supporting Data 604. In some aspects, the particular Collision-Resistant Hash Function 606 can be defined in the Variant Specific Supporting Data 604. In other aspects, a random value can also added to the Variant Specific Supporting Data 222, e.g., to reduce likelihood of unintended decryption.

The Hash Values 607 form the Merkle Tree Leaf Nodes 610 of the Merkle Tree Architecture 608. The Merkle Tree Leaf Nodes can be ordered in a predefined, reproducible manner. Pairs of Merkle Tree Leaf Nodes 610 can be concatenated, and the value can be further hashed into Merkle Tree Non-Leaf Nodes 612 by a Collision Resistant Hashing Function. The process can be repeated until a single Merkle Tree Root 614 is calculated. The Merkle Tree Root 614 can then be submitted to a Time-stamped Distributed Public Ledger 618.

As would be appreciated by a person skilled in the art, the number of individual Variant Specific Supporting Data 604 entries that can be included in a Merkle Tree Architecture 608 may be restricted by the Merkle Tree Depth 616. For example, a Merkle Tree Depth 616 of 5 would allow for only 32 Merkle Tree Leaf Nodes. Hence, by restricting the Merkle Tree Depth 616, the Merkle Tree Architecture 608 naturally restricts the number of Variant Specific Supporting Data 604 that can be attributed to a single Merkle Tree Root 614 in a Time Stamped Distributed Public Ledger 618. As a result, a Merkle Tree Architecture with a fixed and publicized Merkle Tree Depth 616 passively limits bad actors, e.g, from attempting to store every combination and/or enumeration of Variant Specific Supporting Data 604. For example, a bad actor could store a Variant Specific Supporting Data 604 entry claiming that Molecular Variant P871L is Pathogenic, and another Variant Specific Supporting Data 604 entry claiming that the same molecular variant is Benign. A limited Merkle Tree Depth for a particular defined Variant Scope 603 thus can prevent a bad actor from attributing all possible predictions for particular variants to the public ledger under a single Merkle Tree Root 614. As would be appreciated by a person skilled in the art, the number of possible variants for a Variant Scope 603 could be determined by a third party, who could confirm that the Merkle Tree Depth does not exceed the defined Variant Scope 603.

System 601 for providing a hash security proof demonstrating existence of Variant Specific Supporting Data 620 at a particular timestamp on a public ledger, according to one aspect. System 601 can be performed by processing logic having hardware (e.g., circuitry, dedicated logic, programmable logic, microcode, etc.), software (e.g., instructions executing on a processing device), or a combination thereof. It is to be appreciated that not all steps can be needed to perform the disclosure provided herein. Further, some of the steps can be performed simultaneously, or in a different order than shown in FIG. 6, as will be understood by a person of ordinary skill in the art.

In System 601, the timestamp associated with knowledge embedded in Variant Specific Supporting Data 620 (which could be a specific entry from Variant Specific Supporting Data 604), can be demonstrated with a small fraction of the information used to generate the original Merkle Tree Architecture 608. For example, System 601 provides a Merkle Tree Proof 624 to prove the association of a Variant Specific Supporting Data 620 by mathematically illustrating how to transform Variant Specific Supporting Data 620 using a Collision-Resistant Hashing Function 622 and combining the resulting hash with other hashes to recover the Merkle Tree Root 614, stored in the public ledger with a time stamp. The information returned as proof to a Query for Audit Proof 624 can be composed of four parts—the Merkle Tree Root 616, the Merkle Tree Non-Leaf Nodes 612 adjacent to the path leading to the Merkle Tree Leaf Nodes 610 associated with the Variant Specific Supporting Data 620, the Collision-Resistant Hashing Function 622 used to convert the Variant Specific Supporting Data 620, and finally the content of the Variant Specific Supporting Data 620. With these four parts, a person skilled in the art could rapidly generate a mathematical proof that the Variant Specific Supporting Data 620 is cryptographically associated with the Merkle Tree Root 614 published on the Time-Stamped Distributed Public Ledger 618. Hence, an auditor who makes a Query for Audit Proof 624 to System 601 can rapidly determine that a Variant Specific Supporting Data 620 for one or more variants was generated at or before the timestamp associated with the Merkle Tree Root 614.

The descriptions or predictions of phenotypic impacts of molecular variants for one or more functional elements (or molecules), phenotypes, contexts, or set of variants of interest at a given time obtained using the methods and systems disclosed herein (e.g., the variant interpretation methods, variant interpretation support systems, and variant interpretation terminal systems of the present disclosure) can be used, e.g., as part of diagnostics or treatments. The systems, apparatus, devices, methods and/or computer program products disclosed herein, and/or combinations and sub-combinations thereof, can be used for optimizing the determination of the phenotypic (e.g., clinical or non-clinical) impact (e.g., pathogenicity, functionality, or relative effect) of molecular variants identified in molecular tests, samples, or reports of subjects—such as genotypic (sequence) variants identified in genetic and genomic tests, samples, or reports—by way of regularly incorporating, updating, monitoring, validating, selecting, and auditing the best-performing supporting evidence models for the interpretation of molecular variants across a plurality of evidence classes. Such information can subsequently be used for example to decide whether to treat a patient, cease treatment of a patient, select a patient for treatment, predict the prognosis of a patient, select a certain therapeutic agent, etc.

It should be understood that the methods disclosed below are not limited to clinical treatment, and can be related to lifestyle decisions. For example, in response to a determination about a potential phenotypic impact, the subject could effect changes in diet or lifestyle.

It should be understood that the methods disclosed below are not limited to interpreting single variants across single individuals, and can be related to multiple variants across one or more individuals. For example, ranking the relative phenotypic impact of variants in a cohort of patients in a clinical trial.

It should be understood that the methods disclosed below are not limited to interpreting variants in living individuals. For example, a post-mortem interpretation of an individual's variants can inform heritability risk for the individual's relatives.

As used herein the terms "treat," "treatment," or "treatment of" refers to reducing the potential for a disease, disorder or phenotype, reducing the occurrence a disease, disorder or phenotype, and/or a reduction in the severity of the disease or disorder, preferably, to an extent that the subject no longer suffers discomfort and/or altered function due to it. For example, treating can refer to the ability of a therapy when administered to a subject, to prevent a disease or disorder from occurring and/or to cure or to alleviate a disease symptoms, signs, or causes. Treating also refers to mitigating or decreasing at least one clinical symptom and/or inhibition or delay in the progression of the condition and/or prevention or delay of the onset of a disease or illness. Treatment can also refer to mitigating or addressing indirect effects of a disease, disorder or phenotype, such as by informing family planning decisions. Thus, the terms "treat," "treating" or "treatment of" (or grammatically equivalent terms) refer to both prophylactic and therapeutic treatment regimes.

The methods and systems of the present disclosure can provide a benefit in the diagnosis and/or treatment of a disease, disorder or phenotype. A benefit is not necessarily a cure for a particular disease or disorder, but rather encompasses a result which most typically includes alleviation of the disease, disorder or phenotype, or increased survival, elimination of the disease or disorder, reduction of a symptom associated with the disease or disorder, prevention or alleviation of a secondary disease, disorder or condition resulting from the occurrence of a primary disease, disorder or phenotype, and/or prevention of the disease, disorder or phenotype.

The terms "subject" or "patient" as used herein refer to any subject for whom diagnosis, prognosis, or therapy of a disease, disorder or phenotype is desired. As used herein, the terms "subject" or "patient" include any human or nonhuman organism. The term "nonhuman organism" includes all organisms, such as nonhuman primates, sheep, dogs, cats, horses, cows, bears, chickens, amphibians, reptiles, fish, insects, bacteria, etc.

In certain aspects, the methods and system disclosed herein can be used to make decisions related to the administration of a therapeutic agent, which can be an agent used for preventing, treating, managing, or ameliorating a disease or condition.

The term "therapy" as used herein includes any means for curing, mitigating, or preventing a disease or disorder, including, for example, therapeutic agents, instrumentation, supportive measures, and surgical or rehabilitative procedures. In this respect, the term therapy encompasses any protocol, method and/or therapeutic or diagnostic that can be used in prevention, management, treatment, and/or amelioration of a disease or disorder.

The term "therapeutic agent" as used herein refers to any therapeutically active substance that is administered to a subject having a disease or disorder to produce a desired, usually beneficial, effect. The term therapeutic agent includes, e.g., classical low molecular weight therapeutic agents commonly referred to as small molecule drugs and biologics including but not limited to: antibodies or active fragments thereof, peptides, lipids, protein drugs, protein conjugate drugs, enzymes, oligonucleotides, ribozymes, genetic material, prions, virus, bacteria, and eukaryotic cells. A therapeutic agent can also be a pro-drug, which metabolizes into the desired therapeutically active substance when administered to a subject. In some aspects, the therapeutic agent is a prophylactic agent. In addition, a therapeutic agent can be pharmaceutically formulated. A therapeutic agent can also be a radioactive isotope or agent activated by some other form of energy such as light or ultrasonic energy, or by other circulating molecules that can be systemically administered. A therapeutic agent can also be the process of ameliorating the indirect non-physiological effects of a disease, such as family planning through genetic counseling, or informing a patient or a patient's relative of the heritable risk a variant poses to them.

A "therapeutically effective" amount as used herein is an amount of therapeutic agent that provides some improvement or benefit to a subject having a disease or disorder. Thus, a "therapeutically effective" amount is an amount that provides some alleviation, mitigation, and/or decrease in at least one clinical symptom of the disease or disorder. Those skilled in the art will appreciate that therapeutic effects need not be complete or curative, as long as some benefit is provided to the subject.

As used herein, a "sufficient amount" or "an amount sufficient to" achieve a particular result in a patient having an disease or disorder refers to an amount of a therapeutic agent that is effective to produce a desired effect, which is optionally a therapeutic effect (i.e., by administration of a therapeutically effective amount).

The term "sample" as used herein includes any biological fluid or issue, such as whole blood, serum, muscle, saliva obtained from a subject. Samples include any biological fluid or tissue, such as whole blood, serum, muscle, saliva, urine, synovial fluid, bone marrow, cerebrospinal fluid, nasal secretions, sputum, amniotic fluid, bronchoalveolar lavage fluid, lung tissue, peripheral blood mononuclear cells, total white blood cells, lymph node cells, spleen cells, tonsil cells, or skin. In some specific aspects, that sample is blood or a fraction thereof, muscle, skin, or a combination thereof. Samples can be obtained by any means known in the art. In some aspects, a sample can be derived by taking biological samples from a number of subjects and pooling them or pooling an aliquot of each subjects' biological sample. The pooled sample can be treated as a sample from a single subject. The term sample also includes experimentally separated fractions of all of the preceding. For example, a blood sample can be fractionated into serum or into fractions containing particular types of cells. In some aspects, a sample can be a combination of samples from an individual, such as a combination of a tissue and fluid sample.

In order to apply the methods and systems of the disclosure, samples from a patient can be obtained before or after the administration of a therapy to treat a disease or disorder. In some cases, successive samples can be obtained from the patient after therapy has commenced or after therapy has ceased. Samples can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to the original healthcare provider or yet another healthcare provider, healthcare benefits provider or the patient. Similarly, the measuring/determination of one or more scores, comparisons between scores, evaluation of the scores and treatment decisions can be performed by one or more healthcare providers, healthcare benefits providers, and/or clinical laboratories.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice. A healthcare provider can also refer to the individual or an associate of the individual seeking variant interpretation for the individual, such as in the pursuit of understanding a familial phenotype.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer a therapy to treat a disease or disorder. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/ quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy, commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits provides can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

In particular aspects, the methods disclosed herein include informing the subject of a result, e.g., the phenotypic impact of a molecular variant, obtained according to the methods disclosed herein. The patient can be informed verbally, in writing, and/or electronically. This information can also be recorded in a patient medical record. For example, in various aspects, the diagnostic of a disease or disorder treatable with a specific therapeutic agent is recorded in a medical record. The term "medical record" or "patient medical record" refers to an account of a patient's examination and/or treatment that typically includes one or more of the following: the patient's medical history and complaints, the physician's physical findings, the results of diagnostic tests and procedures, and patient medications and therapeutic procedures. A medical record is typically made by one or more physicians and/or physicians' assistants and it is a written, transcribed or otherwise recorded record and/or history of various illnesses or injuries requiring medical care, and/or inoculations, and/or allergies, and/or treatments, and/or prognosis, and/or frequently health information about parents, siblings, and/or occupation. The record may be reviewed by a physician, e.g., in diagnosing a condition or making a treatment decision.

The medical record can be in paper form and/or can be maintained in a computer-readable medium. The medical record can be maintained by a laboratory, physician's office, a hospital, a healthcare maintenance organization, an insurance company, and/or a personal medical record website. In some aspects, a diagnosis, based at least in part on the methods disclosed herein, is recorded on or in a medical alert article such as a card, a worn article, and/or a radiofrequency identification (RFID) tag. As used herein, the term "worn article" refers to any article that can be worn on a subject's body, including, but not limited to, a tag, bracelet, necklace, arm band, or head band.

The methods disclosed herein also include prescribing, initiating, and/or altering prophylaxis and/or therapy for a disease or disorder. In certain aspects, the methods can entail ordering and/or performing one or more additional assays. For example, a genetic testing may be repeated to rule out a false negative result, and/or one or more additional tests may be performed to monitor the subject's status.

A person skilled in the art would understand that the methods disclosed herein can be used, e.g., in treatment, diagnostic, and monitoring methods, as (i) positive selectors, i.e., a specific action would be taken (e.g., treating a patient having a disease or disorder) after a determination of the potential clinical effect of a genotype; or (ii) negative selectors, i.e., a specific action would be taken (e.g., not treating a patient having a disease or disorder) after a determination of the potential clinical effect of a genotype; or (iii) both positive and negative selectors, for example, a specific treatment could cease and a different treatment could commence after a determination of the potential clinical effect of a genotype.

This disclosure provides a method of treating a patient suspected of having a disease, disorder or phenotype, comprising administering an therapeutic agent to the patient if a determination of the potential clinical effect of a genotype according to the methods disclosed herein indicates that the patient can benefit from treatment with the therapeutic agent.

This disclosure also provides methods and systems to facilitate a determination by a healthcare provider, a healthcare benefits provider, or a clinical laboratory to as to whether a patient will benefit from treatment with an therapeutic agent antagonist if a determination of the potential clinical effect of a genotype according to the method disclosed herein indicates that the patient can benefit from treatment with the therapeutic agent.

The methods provided herein will also facilitate a determination by a healthcare provider, a healthcare benefits provider, or a clinical laboratory to as to whether a patient will benefit from treatment with any other therapeutic agents.

The present disclosure also provides a method of treating a patient having or suspected of having a disease or disorder, comprising administering a therapeutic agent to the patient if the phenotypic impact of a molecular variant identified according the methods disclosed herein indicates that the patient would benefit from such treatment. In some aspects, a sample is obtained from the patient and is submitted for genetic testing, for example, to a clinical laboratory.

Also provided is a method of treating a patient having or suspected of having a disease or disorder comprising (a) submitting a sample taken from the patient for genetic testing; and, (b) administering a therapeutic agent to the patient if the phenotypic impact of a molecular variant identified from said genetic testing according the methods disclosed herein indicates that the patient can benefit from the treatment with the therapeutic agent.

The disclosure also provides a method of treating a patient having or suspected of having a disease or disorder comprising (a) measuring the phenotypic impact of a molecular variant identified according the methods disclosed herein in a sample obtained from a patient having or suspected of having a disease or disorder; (b) determining whether the patient can benefit from the treatment with a therapeutic agent based on the presence/absence of an allelic variant; and, (c) advising a healthcare provider to administer the therapeutic agent to the patient if the allelic variant is present/absent.

In certain aspects, a clinical laboratory (e.g., a genetic testing laboratory) determining the phenotypic impact of a molecular variant identified according to the methods of the present disclosure will advise the healthcare provider as to whether the patient can benefit from treatment with a certain therapeutic agent. In some aspects, the clinical laboratory can advise the healthcare provider as to whether the patient can benefit from the initiation, cessation, or modification of treatment with a certain therapeutic agent.

In some aspects, results of a determination of the phenotypic impact of a molecular variant conducted according to the methods of the present disclosure can be submitted to a healthcare provider or a healthcare benefits provider for determination of whether the patient's insurance will cover treatment with a certain therapeutic agent.

In certain aspects this disclosure provides a method of treating a patient having or suspected of having a disease or disorder comprising: determining, e.g., in a genetic testing laboratory, the phenotypic impact of a molecular variant identified according to the methods of the present disclosure; and advising a healthcare provider to administer a certain therapeutic agent to the patient if the phenotypic impact of the molecular variant identified according the methods disclosed herein indicates that the patient can benefit from the treatment with the therapeutic agent.

In certain aspects, the treatment method can comprise: determining, e.g., in a genetic testing laboratory, the phenotypic impact of a molecular variant identified according to the methods of the present disclosure; determining whether the phenotypic impact of the molecular variant indicates that the patient can benefit from the treatment with a therapeutic agent; and advising a healthcare provider to adjust the dosage of the therapeutic agent if indicated, e.g., to increase or maintain the amount or frequency of the therapeutic agent administered to the patient, to discontinue therapy, or to maintain or reduce the amount or frequency of the therapeutic agent.

In some aspects, in addition to the determination of the phenotypic impact of a molecular variant identified according the methods disclosed herein, the methods disclosed herein can comprise determining, submitting a sample taken from the patient for determination, or instructing a clinical laboratory to conduct additional tests, e.g., to determined the absence or presence and/or expression level and/or activity of a certain biomarker or biomarkers.

The determination of the phenotypic impact of a molecular variant identified according the methods disclosed herein can be used, as discussed above, as part of the treatment of a disease or condition. Furthermore, the determination of the phenotypic impact of a molecular variant identified according the methods disclosed herein can be used, e.g., to select a patient for treatment with a therapeutic agent, to select a therapeutic agent among several potential options for treatment, to select or exclude a patient for a clinical trial, or to determine the prognosis of the patient. In response to the potential phenotypic impact of a molecular variant identified according the methods disclosed herein, a healthcare provider, healthcare benefits provider, or counselor can provide lifestyle advice. E.g., in response to the identification of a molecular variant linked to obesity, a subject may be advised to adjust his or her diet; in response to the identification of a molecular variant linked to lung cancer, a subject may be advise to cease smoking, etc.

In some aspects, results of a determination of the phenotypic impact of a molecular variant can be used in biomolecular engineering, molecular bioengineering, genetic engineering or bioengineering applications by informing the effects of variants on a biomolecule, suggesting alterations to the biomolecule to achieve a particular property, behavior or purpose of the biomolecule, biological system or biomedical technology.

As used herein, the term "biomolecule" includes all molecules, both biologically derived and man-made, such as human and non-human proteins, synthetic proteins, peptides, nucleic acids, or biproducts of these, such as analytes, metabolites, or molecules that interact with these, such as ligands, small molecules, other peptides. For example, the human protein "butyrylcholinesterase" is a protein biomolecule.

As used herein, "biomolecular engineering," "molecular bioengineering," "genetic engineering," or "bioengineering" is used to mean application of principles of biology and the tools of engineering to yield products with specific properties. For example, the human protein "human butyrylcholinesterase" was reengineered to yield a hydrolase of cocaine which was 1390 times more effective than in its original form (Xue et al., Design, preparation, and characterization of high-activity mutants of human butyrylcholinesterase specific for detoxification of cocaine. Molecular pharmacology. 2011).

As used herein, "biological system" is used to mean a biological entity or group of entities, such as a group of microorganisms, a human organ, or group of organs. For example, the epidermis is a biological system.

As used herein, "biomedical technology" is used to mean a technology routed in, partially or wholly based on or inspired by biology. For example, PacBio Sequencing achieves single molecule realtime sequencing using engineering DNA polymerases.

What is claimed is:

1. A computer implemented method for predicting a phenotypic impact of a molecular variant of interest, the method comprising:
   (a) recording an evidence model comprising evidence data, wherein the evidence data comprises objects, algorithms, and/or functions that yield predictions of phenotypic impacts of molecular variants for a target entity;
   (b) determining validation performance data for the evidence model based on production data, wherein the production data represents a first plurality of molecular variants with associated phenotypic impacts derived from clinical data and/or population data, and wherein the validation performance data corresponds to a uniform set of performance metrics computed using the production data;
   (c) determining test performance data for the evidence model based on the evidence data and test data in response to receiving the test data for the evidence model, wherein the test data comprises a second plurality of molecular variants with associated phenotypic impacts derived from clinical data and/or population data, wherein the second plurality of molecular variants are disjoint from the first plurality of molecular variants, and wherein the test performance data corresponds to the uniform set of performance metrics computed using the test data;
   (d) ranking the evidence model in a set of evidence models for the target entity based on the validation performance data and/or the test performance data; and
   (e) providing the predicted phenotypic impact using a best-performing evidence model for the target entity based on the ranking in response to a query for the predicted phenotypic impact of the molecular variant of interest for the target entity from a variant interpretation terminal.

2. The method of claim 1, wherein the target entity comprises a functional element, molecule or molecular variant, and a phenotype of interest.

3. The method of claim 1, wherein the recording of the evidence model comprises generating the evidence model based on the production data.

4. The method of claim 1, further comprising generating a hash value of supporting data for the evidence model, wherein the supporting data is generated from the evidence data, the production data, the test data, the validation performance data, the test performance data, or a combination thereof.

5. The method of claim 1, wherein the production data is received from a clinical knowledgebase.

6. The method of claim 1, wherein the determining the validation performance data comprises:
   (1) calculating a phenotype impact score for one or more molecular variants of the target entity in the production data using the evidence model and a model validation technique; and,
   (2) generating the validation performance data based on the phenotype impact scores using the uniform set of performance metrics.

7. The method of claim 1, wherein the determining the test performance data comprises:
   (1) calculating a phenotype impact score for one or more molecular variants of the target entity in the test data using the evidence model and a model validation technique; and,
   (2) generating the test performance data based on the phenotype impact scores using a the uniform set of performance metrics.

8. The method of claim 3, wherein the generating the evidence model based on the production data uses:
   (i) a machine learning technique;
   (ii) a functional assay;
   (iii) a biophysical simulation; or,
   (iv) a combination thereof.

9. The method of claim 8, wherein the machine learning technique is unsupervised, supervised, or semi-supervised.

10. The method of claim 4, further comprising: providing an auditing record to the variant interpretation terminal, wherein:
    (i) the auditing record references an entry for the supporting data in the database, and
    (ii) the auditing record enables the variant interpretation terminal to audit content of the supporting data and a time of creation of the supporting data.

11. The method of claim 1, wherein the uniform set of performance metrics comprises one or more diagnostic metrics, classification metrics, or regression accuracy metrics.

12. The method of claim 11, wherein the diagnostic metrics comprises one or more of the following: raw accuracy, balanced accuracy, true positive rate, true negative rate, positive predictive value, negative predictive value, true positive, true negative, false positive, false negative, and coverage.

13. A system for predicting a phenotypic impact of a molecular variant of interest, the system comprising:

(i) a memory having computer-readable instructions stored thereon; and
(ii) at least one processor coupled to the memory;
wherein the computer-readable instructions, when executed by the at least one processor, cause the at least one processor to:
(a) record an evidence model comprising evidence data, wherein the evidence data comprises objects, algorithms, and/or functions that yield predictions of phenotypic impacts of molecular variants for a target entity;
(b) determine validation performance data for the evidence model based on production data, wherein the production data represents a first plurality of molecular variants with associated phenotypic impacts derived from clinical data and/or population data, and wherein the validation performance data corresponds to a uniform set of performance metrics computed using the production data;
(c) determine test performance data for the evidence model based on the evidence data and test data in response to receiving the test data for the evidence model, wherein the test data comprises a second plurality of molecular variants with associated phenotypic impacts derived from clinical data and/or population data, wherein the second plurality of molecular variants are disjoint from the first plurality of molecular variants, and wherein the test performance data corresponds to the uniform set of performance metrics computed using the test data;
(d) rank the evidence model in a set of evidence models for the target entity based on the validation performance data and/or the test performance data; and
(e) provide the predicted phenotypic impact using a best-performing evidence model for the target entity based on the ranking in response to a query for the predicted phenotypic impact of the molecular variant of interest for the target entity from a variant interpretation terminal.

14. The system of claim 13, wherein the target entity comprises a functional element, molecule or molecular variant, and a phenotype of interest.

15. The system of claim 13, wherein the computer-readable instructions that cause the at least one processor to record the evidence model comprise computer-readable instructions that cause the at least one processor to generate the evidence model based on the production data.

16. The system of claim 13, wherein the computer-readable instructions, when executed by the at least one processor, further cause the at least one processor to generate a hash value of supporting data for the evidence model, wherein the supporting data is generated from the evidence data, the production data, the test data, the validation performance data, the test performance data, or a combination thereof.

17. The system of claim 13, wherein the computer-readable instructions that cause the at least one processor to determine the validation performance data comprise computer-readable instructions that cause the at least one processor to:
(1) calculate a phenotype impact score for one or more molecular variants of the target entity in the production data using the evidence model and a model validation technique; and,
(2) generate the validation performance data based on the phenotype impact scores using the uniform set of performance metrics.

18. The system of claim 13, wherein the computer-readable instructions that cause the at least one processor to determine the test performance data comprise computer-readable instructions that cause the at least one processor to:
(1) calculate a phenotype impact score for one or more molecular variants of the target entity in the test data using the evidence model and a model validation technique; and,
(2) generate the test performance data based on the phenotype impact scores using the uniform set of performance metrics.

19. The system of claim 13, wherein the uniform set of performance metrics comprises one or more diagnostic metrics, classification metrics, or regression accuracy metrics.

20. The system of claim 19, wherein the diagnostic metrics comprise one or more of the following: raw accuracy, balanced accuracy, true positive rate, true negative rate, positive predictive value, negative predictive value, true positive, true negative, false positive, false negative, and coverage.

* * * * *